(12) United States Patent
Patterson et al.

(10) Patent No.: US 9,974,725 B1
(45) Date of Patent: *May 22, 2018

(54) METHODS FOR TREATING CHEMICALLY RELAXED HAIR

(71) Applicant: L'OREAL, Paris (FR)

(72) Inventors: Kwana Patterson, Clark, NJ (US); Barbara Mitchell, Clark, NJ (US); Anand Mahadeshwar, Scotch Plains, NJ (US)

(73) Assignee: L'OREAL, Paris (FR)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/603,960

(22) Filed: May 24, 2017

Related U.S. Application Data

(63) Continuation of application No. 15/603,889, filed on May 24, 2017.

(51) Int. Cl.
*A61K 8/41* (2006.01)
*A61K 8/36* (2006.01)
*A45D 7/04* (2006.01)

(52) U.S. Cl.
CPC .................. *A61K 8/41* (2013.01); *A45D 7/04* (2013.01); *A61K 8/36* (2013.01)

(58) Field of Classification Search
CPC ............... A61K 8/41; A61K 8/36; A45D 7/04
See application file for complete search history.

(56) References Cited

U.S. PATENT DOCUMENTS

| | | | |
|---|---|---|---|
| 2,261,002 A | 10/1941 | Ritter | |
| 2,271,378 A | 1/1942 | Searle | |
| 2,273,780 A | 2/1942 | Dittmar | |
| 2,375,853 A | 5/1945 | Kirby et al. | |
| 2,388,614 A | 11/1945 | Kirby et al. | |
| 2,454,547 A | 11/1948 | Bock et al. | |
| 2,850,351 A | 9/1958 | Moore et al. | |
| 2,961,347 A | 11/1960 | Floyd | |
| 3,142,623 A | 7/1964 | Zviak et al. | |
| 3,193,464 A | 7/1965 | Edman et al. | |
| 3,206,462 A | 9/1965 | McCarty | |
| 3,227,615 A | 1/1966 | Korden | |
| 3,472,243 A | 10/1969 | Wall et al. | |
| 3,472,840 A | 10/1969 | Stone et al. | |
| 3,589,978 A | 6/1971 | Kamal et al. | |
| 3,632,559 A | 1/1972 | Matter et al. | |
| 3,840,656 A | 10/1974 | Kalopissis et al. | |
| 3,874,870 A | 4/1975 | Green et al. | |
| 3,917,817 A | 11/1975 | Vanlerberghe et al. | |
| 3,929,990 A | 12/1975 | Green et al. | |
| 3,966,904 A | 6/1976 | Green et al. | |
| 4,001,432 A | 1/1977 | Green et al. | |
| 4,003,699 A | 1/1977 | Rose et al. | |
| 4,005,193 A | 1/1977 | Green et al. | |
| 4,013,787 A | 3/1977 | Vanlerberghe et al. | |
| 4,025,617 A | 5/1977 | Green et al. | |
| 4,025,627 A | 5/1977 | Green et al. | |
| 4,025,653 A | 5/1977 | Green et al. | |
| 4,026,945 A | 5/1977 | Green et al. | |
| 4,027,020 A | 5/1977 | Green et al. | |
| 4,031,307 A | 6/1977 | DeMartino et al. | |
| 4,075,136 A | 2/1978 | Schaper | |
| 4,131,576 A | 12/1978 | Iovine et al. | |
| 4,166,894 A | 9/1979 | Schaper | |
| 4,172,887 A | 10/1979 | Vanlerberghe et al. | |
| RE30,199 E | 1/1980 | Rose et al. | |
| 4,189,468 A | 2/1980 | Vanlerberghe et al. | |
| 4,197,865 A | 4/1980 | Jacquet et al. | |
| 4,217,914 A | 8/1980 | Jacquet et al. | |
| 4,240,450 A | 12/1980 | Grollier et al. | |
| 4,277,581 A | 7/1981 | Vanlerberghe et al. | |
| 4,348,202 A | 9/1982 | Grollier et al. | |
| 4,349,532 A | 9/1982 | Vanlerberghe et al. | |
| 4,381,919 A | 5/1983 | Jacquet et al. | |

(Continued)

FOREIGN PATENT DOCUMENTS

DE 1220969 B 7/1966
DE 2359399 A1 6/1975
(Continued)

OTHER PUBLICATIONS

Copending U.S. Appl. No. 15/484,663, filed Apr. 11, 2017.
Copending U.S. Appl. No. 15/339,035, filed Oct. 31, 2016.
International Search Report and Written Opinion for counterpart PCT Application No. PCT/US2016/03172, dated Sep. 19, 2016.
International Search Report and Written Opinion for counterpart PCT Application No. PCT/US2016/063724, dated Feb. 2, 2017.
International Search Report and Written Opinion for counterpart PCT Application No. PCT/US2016/063727, dated Feb. 8, 2017.
International Search Report and Written Opinion for counterpart PCT Application No. PCT/US2016/063732, dated Feb. 6, 2017.
International Search Report and Written Opinion for counterpart PCT Application No. PCT/US2016/063728, dated Feb. 1, 2017.

(Continued)

*Primary Examiner* — David J Blanchard
*Assistant Examiner* — Thurman M Wheeler
(74) *Attorney, Agent, or Firm* — Polsinelli PC

(57) ABSTRACT

The instant disclosure relates to methods for treating chemically relaxed hair. The methods include applying a neutralizing composition to the chemically relaxed hair, the neutralizing composition comprising: at least 0.5 wt. % of at least one carboxylic acid, one or more $C_2$-$C_6$ monoalkanolamines, and water. The neutralizing composition is allowed to remain on the hair for a period of time. The hair is also treated with a neutralizing conditioner, which is a different than the neutralizing composition. The neutralizing conditioner includes: at least 0.5 wt. % of at least one carboxylic acid, one or more $C_2$-$C_6$ monoalkanolamines, one or more cationic surfactants, and water. The neutralizing conditioner is allowed to remain on the hair for a period of time. After treatment with a neutralizing composition and a neutralizing conditioner, the hair may be further treated with a shampoo, a conditioner, a conditioning shampoo, etc., dried, and/or styled.

22 Claims, 3 Drawing Sheets

(56) References Cited

U.S. PATENT DOCUMENTS

| | | |
|---|---|---|
| 4,422,853 A | 12/1983 | Jacquet et al. |
| 4,425,132 A | 1/1984 | Grollier et al. |
| 4,532,950 A | 8/1985 | Lang et al. |
| 4,579,732 A | 4/1986 | Grollier et al. |
| 4,591,610 A | 5/1986 | Grollier |
| 4,608,250 A | 8/1986 | Jacquet et al. |
| 4,761,273 A | 8/1988 | Grollier et al. |
| 4,770,873 A | 9/1988 | Wolfram et al. |
| 4,777,040 A | 10/1988 | Grollier et al. |
| 4,793,993 A | 12/1988 | Siuta-Mangano et al. |
| 4,812,307 A | 3/1989 | Siuta-Mangano |
| 4,834,971 A | 5/1989 | Klenk et al. |
| 4,948,579 A | 8/1990 | Jacquet et al. |
| 4,970,066 A | 11/1990 | Grollier et al. |
| 5,061,289 A | 10/1991 | Clausen et al. |
| 5,143,518 A | 9/1992 | Madrange et al. |
| 5,196,189 A | 3/1993 | Jacquet et al. |
| 5,221,286 A | 6/1993 | Singleton et al. |
| 5,350,572 A | 9/1994 | Savaides et al. |
| 5,356,438 A | 10/1994 | Kim et al. |
| 5,380,340 A | 1/1995 | Neunhoeffer et al. |
| 5,534,267 A | 7/1996 | Neunhoeffer et al. |
| 5,565,216 A | 10/1996 | Cowsar et al. |
| 5,651,960 A | 7/1997 | Chan et al. |
| 5,656,265 A | 8/1997 | Bailey et al. |
| 5,663,366 A | 9/1997 | Neunhoeffer et al. |
| 5,688,291 A | 11/1997 | Said et al. |
| 5,708,151 A | 1/1998 | Mockli |
| 5,766,576 A | 6/1998 | Lowe et al. |
| 5,811,085 A | 9/1998 | Halloran |
| 5,833,966 A | 11/1998 | Samain |
| 5,951,969 A | 9/1999 | Golinski et al. |
| 5,985,803 A | 11/1999 | Rizvi et al. |
| 6,099,592 A | 8/2000 | Vidal et al. |
| 6,173,717 B1 | 1/2001 | Schonert et al. |
| 6,284,003 B1 | 9/2001 | Rose et al. |
| 6,338,741 B1 | 1/2002 | Vidal et al. |
| 6,348,189 B1 | 2/2002 | Tanabe et al. |
| 6,458,906 B1 | 10/2002 | Torgerson et al. |
| 6,515,050 B1 | 2/2003 | Mitsuzuka et al. |
| 6,537,532 B1 | 3/2003 | Torgerson et al. |
| 6,569,412 B2 | 5/2003 | Yamaguchi et al. |
| 6,645,258 B2 | 11/2003 | Vidal et al. |
| 6,706,258 B1 | 3/2004 | Gallagher et al. |
| 6,730,789 B1 | 5/2004 | Birault et al. |
| 6,984,250 B1 | 1/2006 | Legrand et al. |
| 7,041,142 B2 | 5/2006 | Chan et al. |
| 7,044,986 B2 | 5/2006 | Ogawa et al. |
| 7,390,479 B2 | 6/2008 | Sockel et al. |
| 7,598,213 B2 | 10/2009 | Geary et al. |
| 7,815,901 B2 | 10/2010 | Mathonneau et al. |
| 7,972,388 B2 | 7/2011 | Hamilton et al. |
| 8,298,519 B2 | 10/2012 | Adams et al. |
| 8,388,701 B2 | 3/2013 | Uellner et al. |
| 8,513,200 B2 | 8/2013 | Dixon et al. |
| 8,613,913 B2 | 12/2013 | Chang et al. |
| 8,642,659 B2 | 2/2014 | Springer et al. |
| 9,095,518 B2 | 8/2015 | Pressly et al. |
| 9,144,537 B1 | 9/2015 | Pressly et al. |
| 9,175,114 B2 | 11/2015 | Puerta et al. |
| 9,180,086 B2 | 11/2015 | Cabourg et al. |
| 9,320,694 B2 | 4/2016 | Cabourg et al. |
| 9,326,926 B2 | 5/2016 | Pressly et al. |
| 9,498,419 B2 | 11/2016 | Pressly et al. |
| 9,597,273 B2 | 3/2017 | Pressly et al. |
| 9,610,241 B2 | 4/2017 | Cabourg et al. |
| 2001/0042276 A1 | 11/2001 | Kawasoe et al. |
| 2001/0052354 A1 | 12/2001 | Nishibe et al. |
| 2002/0050013 A1 | 5/2002 | Vidal et al. |
| 2002/0155081 A1 | 10/2002 | Coope |
| 2002/0189034 A1 | 12/2002 | Kitabata et al. |
| 2003/0019051 A9 | 1/2003 | Vidal et al. |
| 2003/0049222 A1 | 3/2003 | Akhter et al. |
| 2003/0072962 A1 | 4/2003 | Matsuzaki et al. |
| 2003/0152543 A1 | 8/2003 | Legrand et al. |
| 2004/0034944 A1 | 2/2004 | Legrand et al. |
| 2004/0034946 A1 | 2/2004 | Legrand et al. |
| 2004/0086475 A1 | 5/2004 | Boswell et al. |
| 2004/0088800 A1 | 5/2004 | Cotteret |
| 2004/0181883 A1 | 9/2004 | Legrand et al. |
| 2004/0228580 A1 | 11/2004 | Lee et al. |
| 2005/0036970 A1 | 2/2005 | Sabbagh et al. |
| 2005/0087718 A1 | 4/2005 | Okada |
| 2006/0024257 A1 | 2/2006 | Chang et al. |
| 2006/0228316 A1 | 10/2006 | Cannell et al. |
| 2007/0041921 A1 | 2/2007 | Neill et al. |
| 2007/0067924 A1 | 3/2007 | Beck et al. |
| 2007/0107142 A1 | 5/2007 | Nguyen et al. |
| 2007/0116661 A1 | 5/2007 | Mata |
| 2007/0160560 A1 | 7/2007 | Laurent et al. |
| 2007/0261594 A1 | 11/2007 | Vaskelis et al. |
| 2007/0264208 A1 | 11/2007 | Mougin et al. |
| 2008/0066773 A1 | 3/2008 | Anderson et al. |
| 2008/0138309 A1 | 6/2008 | Malle et al. |
| 2008/0141468 A1 | 6/2008 | Cottert |
| 2008/0187506 A1 | 8/2008 | Carballada et al. |
| 2008/0233072 A1 | 9/2008 | Bureiko et al. |
| 2009/0022681 A1 | 1/2009 | Carballada et al. |
| 2009/0126756 A1 | 5/2009 | Syed et al. |
| 2009/0252697 A1 | 10/2009 | Barbarat et al. |
| 2010/0004391 A1 | 1/2010 | Haddleton et al. |
| 2010/0154140 A1 | 6/2010 | Simonet et al. |
| 2010/0202998 A1 | 8/2010 | Ramos-Stanbury et al. |
| 2010/0303748 A1 | 12/2010 | Hercouet |
| 2011/0061671 A1 | 3/2011 | Neplaz et al. |
| 2011/0256084 A1 | 10/2011 | Dixon et al. |
| 2012/0180807 A1 | 7/2012 | Flohr |
| 2012/0244082 A1 | 9/2012 | Sulzback et al. |
| 2013/0034515 A1 | 2/2013 | Stone et al. |
| 2013/0118996 A1 | 5/2013 | Kaplan |
| 2013/0149274 A1 | 6/2013 | Nguyen et al. |
| 2013/0152959 A1 | 6/2013 | Genain et al. |
| 2013/0172518 A1 | 7/2013 | Huang et al. |
| 2013/0309190 A1 | 11/2013 | Dimotakis et al. |
| 2014/0171354 A1 | 6/2014 | Miralles et al. |
| 2014/0186283 A1 | 7/2014 | Cabourg et al. |
| 2014/0196741 A1 | 7/2014 | Cabourg et al. |
| 2015/0004117 A1 | 1/2015 | Tan et al. |
| 2015/0004119 A1 | 1/2015 | Tan et al. |
| 2015/0034117 A1 | 2/2015 | Pressly et al. |
| 2015/0034119 A1 | 2/2015 | Pressly et al. |
| 2015/0037270 A1 | 2/2015 | Pressly et al. |
| 2015/0037271 A1 | 2/2015 | Pressly et al. |
| 2015/0157544 A1 | 6/2015 | Briggs et al. |
| 2015/0252302 A1 | 9/2015 | Rieth et al. |
| 2015/0283041 A1 | 10/2015 | Benn et al. |
| 2015/0290101 A1 | 10/2015 | Pressly et al. |
| 2015/0297496 A1 | 10/2015 | Kroon et al. |
| 2015/0313816 A1 | 11/2015 | Daubresse |
| 2015/0328102 A1 | 11/2015 | Pressly et al. |
| 2016/0081899 A1 | 3/2016 | Pressly et al. |
| 2016/0175238 A1 | 6/2016 | Shin et al. |
| 2016/0193129 A1 | 7/2016 | Pressly et al. |
| 2016/0235649 A1 | 8/2016 | Streuli |
| 2016/0263003 A1 | 9/2016 | Pressly et al. |
| 2016/0310394 A1 | 10/2016 | Pressly et al. |

FOREIGN PATENT DOCUMENTS

| | | |
|---|---|---|
| DE | 3843892 A1 | 6/1990 |
| DE | 4133957 A1 | 4/1993 |
| DE | 4300320 A1 | 7/1994 |
| DE | 19543988 A1 | 5/1997 |
| DE | 10051773 A1 | 4/2002 |
| DE | 10051774 A1 | 4/2002 |
| DE | 102004052480 A1 | 5/2006 |
| DE | 202015104742 U1 | 10/2015 |
| EP | 0122324 A1 | 10/1984 |
| EP | 0298684 A2 | 1/1989 |
| EP | 0299764 A2 | 1/1989 |
| EP | 0714954 A2 | 6/1996 |
| EP | 0770375 A1 | 5/1997 |
| EP | 0978272 A1 | 2/2000 |
| EP | 1174112 A2 | 1/2002 |

(56) References Cited

FOREIGN PATENT DOCUMENTS

| | | |
|---|---|---|
| EP | 1779896 A2 | 5/2007 |
| EP | 2295029 A1 | 3/2011 |
| EP | 2478892 A1 | 7/2012 |
| FR | 1492597 A | 8/1967 |
| FR | 1583363 A | 10/1969 |
| FR | 2162025 A | 7/1973 |
| FR | 2252840 A1 | 6/1975 |
| FR | 2270846 A1 | 12/1975 |
| FR | 2280361 A2 | 2/1976 |
| FR | 2316271 A1 | 1/1977 |
| FR | 2320330 A1 | 3/1977 |
| FR | 2336434 A1 | 7/1977 |
| FR | 2368508 A2 | 5/1978 |
| FR | 2413907 A1 | 8/1979 |
| FR | 2505348 A1 | 11/1982 |
| FR | 2542997 A1 | 9/1984 |
| FR | 2733749 A1 | 11/1996 |
| FR | 2801308 A1 | 5/2001 |
| FR | 2886136 A1 | 12/2006 |
| FR | 2975899 A1 | 12/2012 |
| FR | 2975900 A1 | 12/2012 |
| GB | 713675 A | 8/1954 |
| GB | 741307 A | 11/1955 |
| GB | 773559 A | 4/1957 |
| GB | 1026978 A | 4/1966 |
| GB | 1125794 A | 8/1968 |
| GB | 1153196 A | 5/1969 |
| GB | 1260451 A | 1/1972 |
| GB | 1546809 A | 5/1979 |
| GB | 1584364 A | 2/1981 |
| JP | 63154611 A | 6/1988 |
| JP | 02-019576 A | 1/1990 |
| JP | H02-138110 A | 5/1990 |
| JP | 05-163124 A | 6/1993 |
| JP | 2006-327994 A | 12/2006 |
| JP | 2009-007283 A | 1/2009 |
| JP | 2010-155823 A | 7/2010 |
| JP | 2015086211 A | 5/2015 |
| KR | 10-2001-0039848 A | 7/2001 |
| KR | 2003-0003970 A | 1/2003 |
| KR | 10-2004-0098688 A | 11/2004 |
| KR | 10-2006-0059564 A | 6/2006 |
| KR | 10-2016-0064420 A | 11/2014 |
| WO | 93/00882 A1 | 1/1993 |
| WO | 93/08787 A2 | 5/1993 |
| WO | 94/08969 A1 | 4/1994 |
| WO | 94/08970 A1 | 4/1994 |
| WO | 95/01152 A1 | 1/1995 |
| WO | 95/01772 A1 | 1/1995 |
| WO | 95/15144 A1 | 6/1995 |
| WO | 96/15765 A1 | 5/1996 |
| WO | 97/24106 A1 | 7/1997 |
| WO | 98/56333 A1 | 12/1998 |
| WO | 01/47486 A1 | 7/2001 |
| WO | WO-0152005 A1 | 7/2001 |
| WO | 02/32383 A2 | 4/2002 |
| WO | 02/32386 A2 | 4/2002 |
| WO | 2006/011771 A1 | 2/2006 |
| WO | 2007/038733 A1 | 4/2007 |
| WO | 2009/024936 A2 | 2/2009 |
| WO | 2010/049434 A2 | 5/2010 |
| WO | 2011/134785 A2 | 11/2011 |
| WO | 2012/080321 A2 | 6/2012 |
| WO | 2012/084532 A2 | 6/2012 |
| WO | 2014/072490 | 11/2012 |
| WO | 2012/164064 A1 | 12/2012 |
| WO | 2014/016407 A1 | 1/2014 |
| WO | 2014/118212 A1 | 8/2014 |
| WO | 2014/125452 A1 | 8/2014 |
| WO | 2014/167508 A1 | 10/2014 |
| WO | 2014/207097 A1 | 12/2014 |
| WO | 2015/017768 A1 | 2/2015 |
| WO | 2015/026994 A1 | 2/2015 |
| WO | 2015/075064 A2 | 5/2015 |
| WO | 2016/179017 | 5/2015 |
| WO | 2015/175986 A2 | 11/2015 |
| WO | 2017/091796 | 11/2015 |
| WO | 2017/091796 A1 | 6/2017 |
| WO | 2017/091797 | 6/2017 |
| WO | 2017/091797 A1 | 6/2017 |
| WO | 2017/091800 | 6/2017 |
| WO | 2017/091800 A1 | 6/2017 |

OTHER PUBLICATIONS

Mintel: "Abundant Volume Conditioner," Alterna Professional Haircare, Database Record No. 2177147, Sep. 2013.
Mintel: "Hair Colourant," Catzy Hair Colourant, Database Record ID 743114, Jul. 2007, 4 pages.
Mintel: "Combing Cream," Devintex Cosmeticos, Database Record No. 1595490, Jul. 2011.
Mintel: "Combing Cream," Devintex Cosmeticos, Database Record No. 1595658, Jul. 2011.
Mintel: "Conditioner," Devintex Cosmeticos, Database Record No. 1595545, Jul. 2011.
Mintel: "Conditioner," Laperie Haircare, Database Record No. 3645337, Feb. 2016.
Mintel: "Conditioner," Laperie Haircare, Database Record No. 3790215, Feb. 2016.
Mintel: "Conditioner," Liqwd, Database Record No. 1172691, Sep. 2009.
Mintel: "Conditioner," TIGI, Database Record No. 1442418, Nov. 2010.
Mintel: "Conditioner," TIGI International, Database Record No. 1445427, Nov. 2010.
Mintel: "Conditioner," TGI International, Database Record No. 3280151, Jul. 2015.
Mintel, "Masque for Beautiful Color," Oribe Hair Care, Database Record No. 1522953, Mar. 2011.
Mintel: "Moisturizing Conditioner," Frederic Fekkai, Datablase Record No. 1507159, Mar. 2011.
Mintel: "Post-Service Perfector," Redken, Database Record No. 4326453, Nov. 2016.
Mintel: "Step-3-Conditioner," L'Oreal, Database Record No. 4353779, Oct. 2016.
Mintel: "Step 3-Conditioner," L'Oreal, Database Record No. 4609117, Feb. 2017.
Olaplex with relaxers, OLAPLEX™, pp. 1-2, Apr. 11, 2017, https://olaplex.es/olaplex-with-relaxers/.
Relaxers, Resource Library, Olaplex Education, pp. 1-2, Apr. 11, 2017, https://help.olpalex.com/detail/relaxers.

METHODS FOR TREATING CHEMICALLY RELAXED HAIR

FIELD OF THE DISCLOSURE

The instant disclosure relates to methods for treating chemically relaxed hair. The methods strengthen the hair, minimize or compensate for damage to the hair, and improve the sensorial properties of the hair by imparting smoothness, softness, suppleness, etc.

BACKGROUND

Many chemical treatments are available for changing the appearance of hair. For example, chemical treatments for permanently straightening or curling the hair are common. Also, hair may be lightened or bleached and oxidative dyes can be used to change the color of the hair. Chemical treatments are popular because their effects are long-lasting and can be drastic. Nonetheless, the biggest drawback to chemical treatments is the strain and damage caused to hair. This is because chemical treatments permanently change the chemical and physical structure of the hair. Chemical treatments can remove moisture from the surface of the hair cuticles resulting in the hair becoming brittle, dry, and more vulnerable to breakage.

Individuals seeking to change the shape of hair often turn to chemical procedures that use chemical relaxer compositions. Chemical relaxer compositions are often used on curly hair. The chemical relaxer compositions make hair easier to straighten by chemically "relaxing" the natural curls. The active agent is often a strong alkali, although some formulations are based on ammonium thioglycolate instead. Hair relaxer compositions are applied to hair at a salon by a professional or in the home by the individual consumer.

Hair fiber is a keratinous material, which is comprised of proteins (polypeptides). Many of the polypeptides in hair fibers are bonded together by disulfide bonds (—S—S—). A disulfide bond may be formed from the reaction of the two sulfhydryl groups (—SH), one on each of two cysteine residues, which results in the formation of a cystine residue. While there may be other types of bonds between the polypeptides in hair fibers, such as ionic salt bonds, the permanent curling and shape of the hair is essentially dependent on the disulfide bonds of cystine residues.

Chemical relaxing processes alter the aforementioned disulfide bonds between polypeptides in hair fibers to form lanthionine [S(CH$_2$CHNH$_2$COOH)$_2$]. Thus, the term "lanthionizing" is often used when referring to the relaxing or straightening of keratin fibers by hydroxide ions. Hair fibers may be relaxed or straightened by disrupting the disulfide bonds of the hair fibers with an alkaline agent or with a reducing agent. The chemical disruption of disulfide bonds with an alkaline agent is generally combined with mechanical straightening of the hair, such as combing, and straightening generally occurs due to changes in the relative positions of opposing polypeptide chains within the hair fiber. This reaction is generally terminated by rinsing and/or application of a neutralizing composition.

The reaction with the alkaline agent is normally initiated by hydroxide ions. Hair relaxing processes proceed via the release of the hydroxide ions, which penetrate the hair fiber and transform cystine residues to lanthionine residues. Chemical relaxer compositions often contain varying proportions of strong water-soluble bases, such as sodium hydroxide (NaOH), or include slightly-soluble metal hydroxides, such as calcium hydroxide (Ca(OH)$_2$), which can be converted in situ to soluble bases, such as guanidine hydroxide. Sodium hydroxide is extremely effective in straightening hair fibers but often causes a decrease in the strength of the hair fibers. Chemical relaxer composition often damage the hair to an extent and cause the hair to lose some of its desirable cosmetic properties such as shine, strength, smoothness, etc. Thus, mechanisms to reduce or prevent damage to hair and for improving the cosmetic properties of hair treated with chemical relaxer compositions are desired.

SUMMARY OF THE DISCLOSURE

The instant disclosure relates to methods for treating chemically relaxed. The methods dramatically improve the quality and durability of the chemically relaxed hair. Damage during the chemical relaxing process is repaired, minimized, and/or compensated for with various compositions used in the methods that restructure, strengthen, and/or protect the keratin fibers of the hair. Hair treated according to the methods is not only strengthened but the hair's cosmetic properties (e.g., softness, smoothness, and discipline) are considerably improved. Furthermore, consumers find the natural look and feel of hair treated according to the methods to be very appealing.

The methods typically include:

applying a neutralizing composition to hair within 24 hours from rinsing a chemical relaxer composition from the hair, the neutralizing composition comprising:

at least 0.5 wt. % of at least one carboxylic acid selected from the group consisting of maleic acid, oxalic acid, malonic acid, malic acid, glutaric acid, citraconic acid, citric acid, glycolic acid, succinic acid, adipic acid, tartaric acid, fumaric acid, sebacic acid, benzoic acid, glyoxylic acid monohydrate, a salt thereof, and a mixture thereof, in particular, maleic acid, malonic acid, a salt thereof, or a mixture thereof;

one or more $C_2$-$C_6$ monoalkanolamines, in particular, monoethanolamine; and water;

allowing the neutralizing composition to remain on the hair for a period of time (e.g., about 10 seconds to about 30 minutes, about 5 minute to about 15 minutes, or about 8 to about 12 minutes);

after allowing the neutralizing composition to remain on the hair for a period of time, without rinsing the neutralizing composition from the hair, applying a neutralizing conditioner, the neutralizing conditioner comprising:

at least 0.5 wt. % of at least one carboxylic acid selected from the group consisting of maleic acid, oxalic acid, malonic acid, malic acid, glutaric acid, citraconic acid, citric acid, glycolic acid, succinic acid, adipic acid, tartaric acid, fumaric acid, sebacic acid, benzoic acid, glyoxylic acid monohydrate, and a mixture thereof, in particular, maleic acid, malonic acid, a salt thereof, or a mixture thereof;

one or more $C_2$-$C_6$ monoalkanolamines, in particular, monoethanolamine;

one or more cationic surfactants; and water;

allowing the neutralizing conditioner to remain on the hair for a period of time (e.g., about 10 seconds to about 30 minutes, about 5 minute to about 15 minutes, or about 8 to about 12 minutes); and after allowing the neutralizing conditioner to remain on the hair for a period of time, rinsing the neutralizing conditioner and the neutralizing composition from the hair.

After rinsing the neutralizing conditioner and the neutralizing composition from the hair, the hair may further shampooed with a shampoo and/or conditioned with a conditioner. Also, the hair may be subsequently dried and styled, for example, the hair may be dried with a blow dryer and/or styled with a hot iron.

The neutralizing composition and the neutralizing conditioner are not identical compositions although they may both include identical carboxylic acid(s) and/or identical $C_2$-$C_6$ monoalkanolamines. The neutralizing conditioner typically differs from the neutralizing composition by including components that provide conditioning properties to the hair, for example, cationic surfactants, cationic polymers, water-soluble solvents, fatty compounds, etc. The neutralizing composition provides initial neutralization of the pH of the chemically relaxed hair, i.e., the neutralizing composition reduces the alkaline pH of chemically relaxed hair (pH of about 8-10) to an acidic pH of less than 7. Although the neutralizing conditioner continues to neutralize the pH of the hair (i.e., continues to reduce the pH of the hair), it additionally provides conditioning, strengthening, and other desirable properties to the hair.

The ratio of the total amount of the at least one carboxylic acid, a salt thereof, or mixture thereof in the neutralizing composition to the total amount of the one or more $C_2$-$C_6$ monoalkanolamines in the neutralizing composition is about 1:1 to about 5:1, about 1:1 to about 4:1, or about 1:1 to about 3:1. Likewise, the ratio of the total amount of the at least one carboxylic acid, a salt thereof, or mixture thereof in the neutralizing composition to the total amount of the one or more $C_2$-$C_6$ monoalkanolamines in the neutralizing composition is about 1:1 to about 5:1, about 1:1 to about 4:1, or about 1:1 to about 3:1.

The total amount of the one or more carboxylic acids in the neutralizing composition and/or the neutralizing conditioner may vary but is typically at least 0.5 to about 10 wt. %, about 1 to about 8 wt. %, or about 1 to about 6 wt. %, based on the total weight of the neutralizing composition. The total amount of the one or more $C_2$-$C_6$ monoalkanolamines in the neutralizing composition may vary but is typically about 0.1 to about 10 wt. %, about 0.1 to about 8 wt. %, or about 0.5 to about 6 wt. %, based on the total weight of the neutralizing composition.

The total amount of the one or more carboxylic acids in the neutralizing conditioner and/or the neutralizing conditioner may vary but is typically at least 0.5 to about 10 wt. %, about 1 to about 8 wt. %, or about 1 to about 6 wt. %, based on the total weight of the neutralizing conditioner. The total amount of the one or more $C_2$-$C_6$ monoalkanolamines in the neutralizing conditioner may vary but is typically about 0.1 to about 10 wt. %, about 0.1 to about 8 wt. %, or about 0.5 to about 6 wt. %, based on the total weight of the neutralizing conditioner.

The various composition used in the disclosed methods may be included in kits. For example, a kit may include a neutralizing composition and a neutralizing conditioner, wherein each composition is separately contained. In some cases, the kit may additionally include a chemical reducing composition. In some cases, the kits may also include a shampooing and/or cleansing composition (e.g., a shampoo, a conditioner (different than the neutralizing conditioner), a conditioning shampoo (all-in-one shampoo/conditioner), etc.). Instructions, mixing components, brushes, gloves, measuring tools, etc., may also be included in the kits.

As mentioned previously, the methods of the disclosure dramatically improve the quality and durability of the chemically relaxed hair. Accordingly, the disclosure relates to methods for repairing, minimizing, and/or compensating for damage to chemically relaxed hair. Moreover, the methods relate to restructuring, strengthening, and/or rejuvenating the keratin fibers of hair. In particular, the methods improve the Young's modulus of the hair and/or improve the break stress of the hair. Therefore, in some instances, the methods relates to increasing a mean Young's modulus of hair and/or increasing the break stress of hair, for example, by at least 5%, 10%, 15%, or more, relative to chemically relaxed hair to which a neutralizing composition and a neutralizing conditioner of the instant disclosure is not applied (i.e., relative to chemically relaxed hair not treated according to the disclosed methods).

BRIEF DESCRIPTION OF THE DRAWINGS

Implementations of the present technology will now be described, by way of example only, with reference to the attached figures, wherein.

Figure 1:
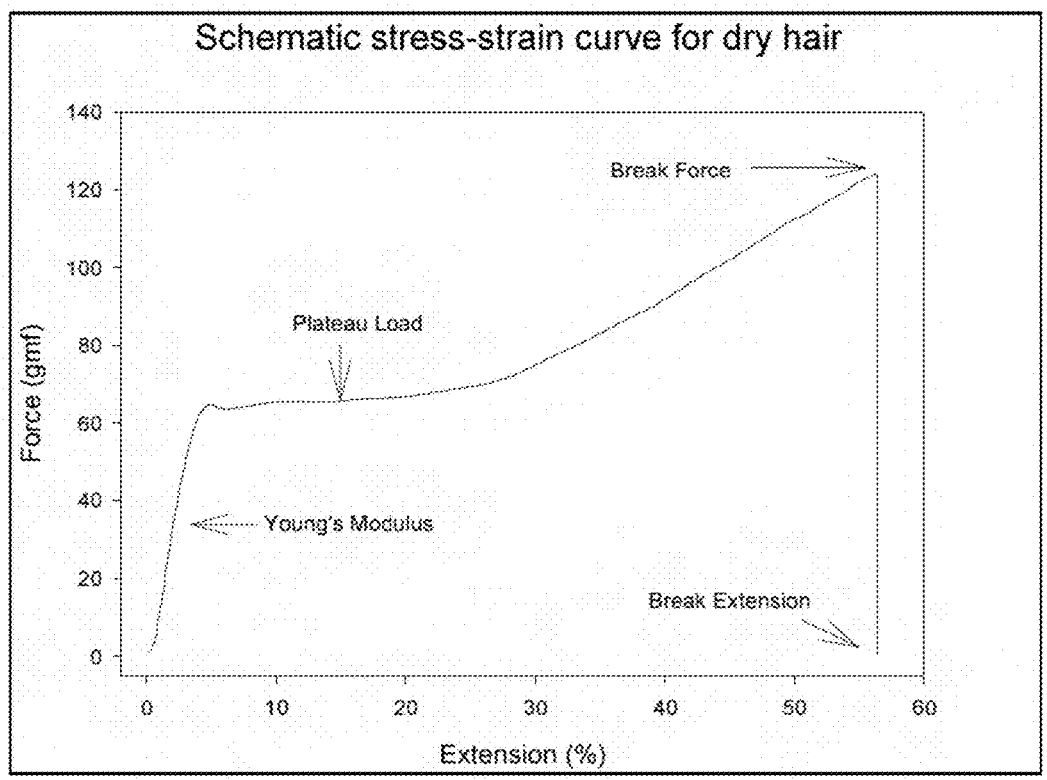
FIG. 1 is a typical stress-strain curve for dry hair with arrows identifying which part of the curve relates to the Young's modulus, the plateau load, the break force, and the break extension.

It should be understood that the various aspects are not limited to the arrangements and instrumentality shown in the drawings.

DETAILED DESCRIPTION OF THE DISCLOSURE

The methods of the instant disclosure involve treating chemically relaxed hair with a sequence of unique hair-treatment compositions that neutralize, strengthen, and improve the cosmetic properties of the hair. For example, after a chemical relaxer composition is rinsed from the hair, the hair is treated with a neutralizing composition for a period of time followed by a treatment with a neutralizing conditioner for a period of time. After rinsing the neutralizing composition and the neutralizing conditioner from the hair, the hair may be subjected to a regular shampooing and optional conditioning routine, dried, and styled.

More specifically, the methods include:
applying a neutralizing composition to hair within about 24, 6, or 1 hour(s) from rinsing a chemical relaxer composition from the hair, the neutralizing composition comprising:
at least 0.5 wt. % of at least one carboxylic acid selected from the group consisting of maleic acid, oxalic acid, malonic acid, malic acid, glutaric acid, citraconic acid, citric acid, glycolic acid, succinic acid, adipic acid, tartaric acid, fumaric acid, sebacic acid, benzoic acid, glyoxylic acid monohydrate, a salt thereof, and a mixture thereof, in particular, maleic acid, malonic acid, a salt thereof, and a mixture thereof;

one or more $C_2$-$C_6$ monoalkanolamines, in particular, monoethanolamine; and water;

allowing the neutralizing composition to remain on the hair for a period of time (e.g., about 10 seconds to about 30 minutes, about 5 minute to about 15 minutes, or about 8 to about 12 minutes);

after allowing the neutralizing composition to remain on the hair for a period of time, without rinsing the neutralizing composition from the hair, applying a neutralizing conditioner (the neutralizing conditioner being a different composition than the neutralizing composition), the neutralizing conditioner comprising:

at least 0.5 wt. % of at least one carboxylic acid selected from the group consisting of maleic acid, oxalic acid, malonic acid, malic acid, glutaric acid, citraconic acid, citric acid, glycolic acid, succinic acid, adipic acid, tartaric acid, fumaric acid, sebacic acid, benzoic acid, glyoxylic acid monohydrate, and a mixture thereof, in particular, maleic acid, malonic acid, a salt thereof, or a mixture thereof;

one or more $C_2$-$C_6$ monoalkanolamines, in particular, monoethanolamine;

one or more cationic surfactants; and water;

allowing the neutralizing conditioner to remain on the hair for a period of time (e.g., about 10 seconds to about 30 minutes, about 5 minute to about 15 minutes, or about 8 to about 12 minutes); and after allowing the neutralizing conditioner to remain on the hair for a period of time, rinsing the neutralizing conditioner and the neutralizing composition from the hair.

After rinsing the neutralizing conditioner and the neutralizing composition from the hair, the hair may further shampooed with a shampoo and/or conditioned with a conditioner. Also, the hair may be subsequently dried and styled, for example, the hair may be dried with a blow dryer and/or styled with a hot iron.

The neutralizing composition and the neutralizing conditioner are not identical compositions although they may both include identical carboxylic acid(s) and/or identical $C_2$-$C_6$ monoalkanolamines. The neutralizing conditioner typically differs from the neutralizing composition by including components that provide conditioning properties to the hair, for example, cationic surfactants, cationic polymers, water-soluble solvents, fatty compounds, etc. The neutralizing composition provides initial neutralization of the pH of the chemically relaxed hair, i.e., the neutralizing composition reduces the alkaline pH of chemically relaxed hair (pH of about 8-10) to an acidic pH of less than 7. Although the neutralizing conditioner continues to neutralize the pH of the hair (i.e., continues to reduce the pH of the hair), it additionally provides conditioning, strengthening, and other desirable properties to the hair.

The neutralizing composition may be provided as a concentrated composition that is diluted prior to application to the hair. A concentrated neutralizing composition may be diluted, for example, with water prior to application to the hair. In some instances, the concentrated neutralizing composition is diluted with water in a ratio of about 1:1 to about 1:10 (concentrated neutralizing composition:water). The dilution ratio may also be about 1:2 to about 1:8, about 1:3 to about 1:7, about 1:4 to about 1:6, or about 1:6 (i.e., one part concentrated neutralizing composition combined with six parts of water). A non-limiting example of a concentrated neutralizing composition includes:

i. about 1 to about 30 wt. %, about 2 to about 25 wt. %, or about 5 to about 20 wt. % of at least one carboxylic acid selected from the group consisting of maleic acid, oxalic acid, malonic acid, malic acid, glutaric acid, citraconic acid, citric acid, glycolic acid, succinic acid, adipic acid, tartaric acid, fumaric acid, sebacic acid, benzoic acid, glyoxylic acid monohydrate, a salt thereof, and a mixture thereof, in particular, maleic acid, malonic acid, a salt thereof, and a mixture thereof, in particular, maleic acid, malonic acid, a salt thereof, and a mixture thereof;
 ii. about 1 to about 20 wt. %, about 1 to about 15 wt. %, or about 2 to about 10 wt. % of one or more $C_2$-$C_6$ monoalkanolamines, in particular, monoethanolamine; and
 iii. about 50 to about 95 wt. %, about 60 to about 90, or about 70 to about 90 wt. % of water.

The neutralizing composition may include additional components, for example, water-soluble solvents, thickening agents, preservatives, perfumes, etc. Nonetheless, additional components are not required and may be excluded. Non-limiting examples of additional components that may be included in the hair-treatment compositions are provided later, under headings such as, "Water-Soluble Solvents," "Thickening Agents," etc.

The neutralizing composition is often provided in the form of a liquid, but may be in the form of a gel, a foam, a lotion, a cream, a mousse, an emulsion, etc. A concentrated neutralizing composition in the form of a liquid, for example, can be diluted with water and applied to the hair with a spray bottle.

The ratio of the total amount of the at least one carboxylic acid, a salt thereof, or mixture thereof in the neutralizing composition to the total amount of the one or more $C_2$-$C_6$ monoalkanolamines in the neutralizing composition is about 1:1 to about 5:1, about 1:1 to about 4:1, or about 1:1 to about 3:1. The ratio applies regardless of whether the neutralizing composition is concentrated or diluted (ready-to-use), as dilution does not influence the ratio of the carboxylic acid, a salt thereof, or mixture thereof to the one or more $C_2$-$C_6$ monoalkanolamines.

The total amount of the one or more carboxylic acids in the neutralizing composition when applied to the hair (after being diluted or when provided as a ready-to-use composition) may vary but is typically at least 0.5 to about 10 wt. %, about 1 to about 8 wt. %, or about 1 to about 6 wt. %, based on the total weight of the neutralizing composition. In some cases, the total amount of the one or more carboxylic acids in the neutralizing composition is at least 0.5 to about 10 wt. %, at least 0.5 to about 8 wt. %, at least 0.5 to about 6 wt. %, at least 0.5 to about 4 wt. %, about 0.5 to about 2 wt. %, about 1 to about 10 wt. %, about 1 to about 8 wt. %, about 1 to about 6 wt. %, about 1 to about 4 wt. %, or about 1 to about 2 wt. %.

The total amount of the one or more $C_2$-$C_6$ monoalkanolamines in the neutralizing composition when applied to the hair (after being diluted or when provided as a ready-to-use composition) may vary but is typically about 0.1 to about 10 wt. %, about 0.1 to about 8 wt. %, or about 0.5 to about 6 wt. %, based on the total weight of the neutralizing composition. In some cases, the total amount of the one or more $C_2$-$C_6$ monoalkanolamines is about 0.1 to about 10 wt. %, about 0.1 to about 8 wt. %, about 0.1 to about 6 wt. %, about 0.1 to about 4 wt. %, about 0.1 to about 2 wt. %, about 0.1 to about 1 wt. %, about 0.3 to about 10 wt. %, about 0.3 to about 8 wt. %, about 0.3 to about 6 wt. %, about 0.3 to about 4 wt. %, about 0.3 to about 2 wt. %, about 0.3 to about 1 wt. %, about 0.5 to about 10 wt. %, about 0.5 to about 8 wt. %, about 0.5 to about 6 wt. %, about 0.5 to about 4 wt. %, about 0.5 to about 2 wt. %, or about 0.5 to about 1 wt. %.

The total amount of water in the neutralizing composition when applied to the hair (after being diluted or when provided as a ready-to-use composition) may vary but is typically about 50 to about 99 wt. %, about 60 to about 98 wt. %, or about 70 to about 98 wt. %, based on the total weight of the neutralizing composition. In some cases, the total amount of water may be about 50 to 99 wt. %, about 60 to about 99 wt. %, about 70 to about 99 wt. %, about 80 to about 99 wt. %, about 85 to about 99 wt. %, about 60 to about 98 wt. %, about 70 to about 98 wt. %, about 80 to about 98 wt. %, about 85 to about 98 wt. %, or about 80 to about 97 wt. %.

The neutralizing conditioners used in the methods typically include:
  i. at least 0.5 wt. % of at least one carboxylic acid selected from the group consisting of maleic acid, oxalic acid, malonic acid, malic acid, glutaric acid, citraconic acid, citric acid, glycolic acid, succinic acid, adipic acid, tartaric acid, fumaric acid, sebacic acid, benzoic acid, glyoxylic acid monohydrate, and a mixture thereof, in particular, maleic acid, malonic acid, a salt thereof, or a mixture thereof;
  ii. one or more $C_2$-$C_6$ monoalkanolamines, in particular, monoethanolamine;
  iii. one or more cationic surfactants; and
  iv. water.

The neutralizing condition may include additional components such as, for example, fatty compounds, water-soluble solvents, cationic polymers, thickening agents, pH adjusters, preservatives, perfumes, etc. The neutralizing conditioner may be provided in the form of a liquid, a gel, a foam, a lotion, a cream, a mousse, an emulsion, etc.

The ratio of the total amount of the at least one carboxylic acid, a salt thereof, or mixture thereof in the neutralizing conditioner to the total amount of the one or more $C_2$-$C_6$ monoalkanolamines in the neutralizing conditioner is about 1:1 to about 5:1, about 1:1 to about 4:1, or about 1:1 to about 3:1.

The total amount of the one or more carboxylic acids in the neutralizing conditioner may vary but is typically at least 0.5 to about 10 wt. %, about 1 to about 8 wt. %, or about 1 to about 6 wt. %, based on the total weight of the neutralizing conditioner. In some cases, the total amount of the one or more carboxylic acids in the neutralizing conditioner is at least 0.5 to about 10 wt. %, at least 0.5 to about 8 wt. %, at least 0.5 to about 6 wt. %, at least 0.5 to about 4 wt. %, about 0.5 to about 2 wt. %, about 1 to about 10 wt. %, about 1 to about 8 wt. %, about 1 to about 6 wt. %, about 1 to about 4 wt. %, or about 1 to about 2 wt. %.

The total amount of the one or more $C_2$-$C_6$ monoalkanolamines in the neutralizing conditioner may vary but is typically about 0.1 to about 10 wt. %, about 0.1 to about 8 wt. %, or about 0.5 to about 6 wt. %, based on the total weight of the neutralizing conditioner. In some cases, the total amount of the one or more $C_2$-$C_6$ monoalkanolamines is about 0.1 to about 10 wt. %, about 0.1 to about 8 wt. %, about 0.1 to about 6 wt. %, about 0.1 to about 4 wt. %, about 0.1 to about 2 wt. %, about 0.1 to about 1 wt. %, about 0.3 to about 10 wt. %, about 0.3 to about 8 wt. %, about 0.3 to about 6 wt. %, about 0.3 to about 4 wt. %, about 0.3 to about 2 wt. %, about 0.3 to about 1 wt. %, about 0.5 to about 10 wt. %, about 0.5 to about 8 wt. %, about 0.5 to about 6 wt. %, about 0.5 to about 4 wt. %, about 0.5 to about 2 wt. %, or about 0.5 to about 1 wt. %.

Many cationic surfactants are well-known and may be used in the neutralizing conditioner. Non-limiting examples of cationic surfactants include cetrimonium chloride, cetrimonium methosulfate, stearimonium chloride, behentrimonium chloride, behentrimonium methosulfate, behenamidopropyltrimonium methosulfate, stearamidopropyltrimonium chloride, arachidtrimonium chloride, distearyldimonium chloride, dicetyldimonium chloride, tricetylmonium chloride, oleamidopropyl dimethylamine, linoleamidopropyl dimethylamine, isostearamidopropyl dimethylamine, stearamidopropyl dimethylamine, oleyl hydroxyethyl imidazoline, stearamidopropyldimethylamine, behenamidopropyldimethylamine, behenamidopropyldiethylamine, behenamidoethyldiethyl-amine, behenamidoethyldimethylamine, arachidamidopropyldimethylamine, arachidamido-propyidiethylamine, arachidamidoethyidiethylamine, arachidamido-ethyidimethylamine, myristamidopropyl PG-dimonium chloride phosphate, brassicyl isoleucinate esylate, and a mixture thereof. In some cases, the neutralizing conditioner includes at least cetrimonium chloride, behentrimonium methosulfate, stearamidopropyl dimethylamine, quaternium-91, and a mixture thereof.

A more exhaustive list of cationic surfactants that may be included in the hair-treatment compositions is provided later, under the heading "Cationic Surfactants."

The total amount of the one or more cationic surfactants may vary but is typically about 0.1 to about 20 wt. %, about 0.5 to about 15 wt. %, or about 1 to about 10 wt. %, based on the total amount of the conditioning composition. In some cases, the total amount of the one or more cationic surfactants may be about 0.1 to about 8 wt. %, about 0.1 to about 6 wt. %, about 0.1 to about 5 wt. %, about 0.5 to about 10 wt. %, about 0.5 to about 8 wt. %, about 0.5 to about 6 wt. %, or about 0.5 to about 5 wt. %.

The total amount of water in the neutralizing conditioner may vary but is typically about 50 to about 95 wt. %, about 60 to about 92 wt. %, or about 70 to about 90 wt. %, based on the total weight of the neutralizing conditioner. In some cases, the total amount of water may be about 50 to about 95 wt. %, about 55 to about 95 wt. %, about 60 to about 95 wt. %, about 65 to about 95 wt. %, about 70 to about 95 wt. %, about 75 to about 95 wt. %, about 80 to about 95 wt. %, about 60 to about 92 wt. %, about 70 to about 92 wt. %, about 80 to about 92 wt. %, about 60 to about 90 wt. %, about 70 to about 90 wt. %, or about 80 to about 90 wt. %.

The neutralizing conditioner may include one or more fatty compounds. Non-limiting examples of fatty compounds include oils, mineral oil, fatty alcohols, fatty acids, alkyl ethers of fatty alcohols, fatty acid esters of fatty alcohols, fatty acid esters of alkyl ethers of fatty alcohols, fatty acid esters of alkoxylated fatty alcohols, fatty acid esters of alkyl ethers of alkoxylated fatty alcohols, hydroxy-substituted fatty acids, and a mixture thereof. In some cases, the conditioning composition includes at least mineral oil, cetearyl alcohol, or a mixture thereof. A more exhaustive list of fatty compounds that may be included in the neutralizing conditioner is provided later, under the heading "Fatty Compounds."

The total amount of the one or more fatty compounds may be about 0.1 to about 40 wt. %, based on the total weight of the neutralizing conditioner. In some cases, the total amount of the one or more fatty compounds may be about 0.1 to about 30 wt. %, about 0.1 to about 20 wt. %, about 0.1 to about 20 wt. %, about 0.1 to about 10 wt. %, about 1 wt. % to about 40 wt. %, about 1 wt. % to about 30 wt. %, about 1 wt. % to about 20 wt. %, or about 1 wt. % to about 10 wt. %.

Water-soluble solvents may be included in the neutralizing conditioner. The term "water-soluble solvent" is interchangeable with the term "water-miscible solvent" and means a compound that is liquid at 25° C. and at atmospheric pressure (760 mmHg), and it has a solubility of at least 50% in water under these conditions. In some cases, the water soluble solvents has a solubility of at least 60%, 70%, 80%, or 90%. Non-limiting examples of water-soluble solvents include, for example, glycerin, $C_{1-4}$ alcohols, organic solvents, fatty alcohols, fatty ethers, fatty esters, polyols, glycols, vegetable oils, mineral oils, liposomes, laminar lipid materials, or any a mixture thereof. As examples of organic solvents, non-limiting mentions can be made of monoalcohols and polyols such as ethyl alcohol, isopropyl alcohol, propyl alcohol, benzyl alcohol, and phenylethyl alcohol, or glycols or glycol ethers such as, for example, monomethyl, monoethyl and monobutyl ethers of ethylene glycol, propylene glycol or ethers thereof such as, for example, monomethyl ether of propylene glycol, butylene glycol, hexylene glycol, dipropylene glycol as well as alkyl ethers of diethylene glycol, for example monoethyl ether or monobutyl ether of diethylene glycol. Other suitable examples of organic solvents are ethylene glycol, propylene glycol, butylene glycol, hexylene glycol, propane diol, and glycerin. The organic solvents can be volatile or non-volatile compounds.

Further non-limiting examples of water-soluble solvents which may be used include alkanediols (polyhydric alcohols) such as glycerin, 1,2,6-hexanetriol, trimethylolpropane, ethylene glycol, propylene glycol, diethylene glycol, triethylene glycol, tetraethylene glycol, pentaethylene glycol, dipropylene glycol, 2-butene-1,4-diol, 2-ethyl-1,3-hexanediol, 2-methyl-2,4-pentanediol, (caprylyl glycol), 1,2-hexanediol, 1,2-pentanediol, and 4-methyl-1,2-pentanediol; alkyl alcohols having 1 to 4 carbon atoms such as ethanol, methanol, butanol, propanol, and isopropanol; glycol ethers such as ethylene glycol monomethyl ether, ethylene glycol monoethyl ether, ethylene glycol monobutyl ether, ethylene glycol monomethyl ether acetate, diethylene glycol monomethyl ether, diethylene glycol monoethyl ether, diethylene glycol mono-n-propyl ether, ethylene glycol mono-iso-propyl ether, diethylene glycol mono-iso-propyl ether, ethylene glycol mono-n-butyl ether, ethylene glycol mono-t-butyl ether, diethylene glycol mono-t-butyl ether, 1-methyl-1-methoxybutanol, propylene glycol monomethyl ether, propylene glycol monoethyl ether, propylene glycol mono-t-butyl ether, propylene glycol mono-n-propyl ether, propylene glycol mono-iso-propyl ether, dipropylene glycol monomethyl ether, dipropylene glycol monoethyl ether, dipropylene glycol mono-n-propyl ether, and dipropylene glycol mono-iso-propyl ether; 2-pyrrolidone, N-methyl-2-pyrrolidone, 1,3-dimethyl-2-imidazolidinone, formamide, acetamide, dimethyl sulfoxide, sorbit, sorbitan, acetine, diacetine, triacetine, sulfolane, and a mixture thereof.

In some cases, the water-soluble solvent may be selected from the group consisting of one or more glycols, $C_{1-4}$ alcohols, glycerin, and a mixture thereof. In some cases, the water-soluble solvent is selected from the group consisting of hexylene glycol, propene glycol, caprylyl glycol, glycerin, isopropyl alcohol, and a mixture thereof.

Polyhydric alcohols are useful. Examples of polyhydric alcohols include glycerin, ethylene glycol, diethylene glycol, triethylene glycol, propylene glycol, dipropylene glycol, tripropylene glycol, 1,3-butanediol, 2,3-butanediol, 1,4-butanediol, 3-methyl-1,3-butanediol, 1,5-pentanediol, tetraethylene glycol, 1,6-hexanediol, 2-methyl-2,4-pentanediol, polyethylene glycol, 1,2,4-butanetriol, 1,2,6-hexanetriol, and a mixture thereof. Polyol compounds may also be used. Non-limiting examples include the aliphatic diols, such as 2-ethyl-2-methyl-1,3-propanediol, 3,3-dimethyl-1,2-butanediol, 2,2-diethyl-1,3-propanediol, 2-methyl-2-propyl-1,3-propanediol, 2,4-dimethyl-2,4-pentanediol, 2,5-dimethyl-2,5-hexanediol, 5-hexene-1,2-diol, and 2-ethyl-1,3-hexanediol, and a mixture thereof.

A more exhaustive list of water-soluble solvents that may be included in the neutralizing conditioner is provided later, under the heading "Water-Soluble Solvents."

The total amount of the one or more water-soluble solvents in the neutralizing conditioner may vary, but in some cases are about 0.1 to about 50 wt. %, about 0.5 to about 30 wt. %, or about 1 to about 15 wt. %, based on the total weight of the neutralizing conditioner. The total amount of the one or more water-soluble solvents may be about 0.1 to about 40 wt. %, about 0.1 to about 30 wt. %, about 0.1 to about 20 wt. %, about 0.1 to about 20 wt. %, about 0.1 to about 10 wt. %, about 0.1 to about 5 wt. %, about 1 to about 50 wt. %, about 1 to about 40 wt. %, about 1 to about 30 wt. %, about 1 to about 20 wt. %, about 1 to about 10 wt. %, or about 1 to about 5 wt. %.

One or more thickening agents may also be included in the neutralizing conditioner. Non-limiting examples of thickening agents include carboxylic acid/carboxylate copolymers, hydrophobically-modified cross-linked copolymers of carboxylic acid and alkyl carboxylate vinyl polymers, cross linked acrylic acid polymers (carbomer), methyl cellulose, ethyl cellulose, hydroxyethyl cellulose, hydroxylpropyl cellulose, hydroxypropyl methyl cellulose, nitro cellulose, sodium cellulose sulfate, sodium carboxymethyl cellulose, crystalline cellulose, cellulose powder, polyvinylpyrrolidone, polyvinyl alcohol, guar gum, hydroxypropyl guar gum, xanthan gum, arabic gum, tragacanth gum, carob gum, karaya gum, carrageenan, pectin, agar, starch, algae colloids, starch-based polymers, methylhydroxypropyl starch, alginic acid-based polymers, propylene glycol esters, sodium polyacrylate, polyethylacrylate, polyacrylamide, polyethyleneimine, bentonite, aluminum magnesium silicate, laponite, hectonite, anhydrous silicic acid, and a mixture thereof. In some cases, the one or more thickening agents are selected from the group consisting of cross linked acrylic acid polymers (carbomer), methyl cellulose, ethyl cellulose, hydroxyethyl cellulose, hydroxypropyl methyl cellulose, hydroxylpropyl cellulose, sodium carboxymethyl cellulose, polyvinylpyrrolidone, polyvinyl alcohol, guar gum, hydroxypropyl guar gum, xanthan gum, arabic gum, carrageenan, starch-based polymers, and a mixture thereof. In some cases, the neutralizing conditioner includes at least hydroxylpropyl cellulose.

A more exhaustive list of thickening agents that may be included in the neutralizing conditioner is provided later, under the heading "Thickening Agents."

The total amount of the one or more thickening agents can vary but is typically about 0.01 to about 10 wt. %, 0.05 to about 5 wt. %, or about 0.1 to about 4 wt. %, based on the total weight of the neutralizing conditioner. The total amount of the one or more thickening agents may be about 0.01 to about 8 wt. %, about 0.01 to about 6 wt. %, about 0.01 to about 5 wt. %, about 0.1 to about 10 wt. %, about 0.1 to about 8 wt. %, about 0.1 to about 6 wt. %, about 0.1 to about 5 wt. %, about 0.5 to about 10 wt. %, about 0.5 to about 8 wt. %, about 0.5 to about 6 wt. %, or about 0.5 to about 5 wt. %.

In some cases, the neutralizing conditioner may include one or more cationic polymers. Non-limiting examples of cationic polymers include poly(methacryloyloxyethyl trimethylammonium chloride), polyquaternium-37, quaternized cellulose derivatives, polyquaternium-4, polyquaternium-10, polyquaternium-11, cationic alkyl polyglycosides, cationized honey, cationic guar derivatives, polymeric dimethyl diallyl ammonium salts and copolymers thereof with esters and amides of acrylic acid and methacrylic acid, copolymers of vinyl pyrrolidone with quaternized derivatives of dialkylaminoalkyl acrylate and methacrylate, vinyl pyrrolidone-vinyl imidazolium methochloride copolymers, quaternized polyvinyl alcohol, polyquaternium-2, polyquaternium-7, polyquaternium-17, polyquaternium-18, polyquaternium-24, polyquaternium-27, polyquaternium-72, and a mixture thereof. In some cases, the one or more cationic polymers are polyquaterniums, for example, polyquaternium-11, polyquaternium-37, or a mixture thereof.

A more exhaustive list of cationic polymers that may be included in the neutralizing conditioner is provided later, under the heading "Cationic Polymers."

The total amount of the one or more cationic polymers may vary but it typically about 0.01 to about 10 wt. %, based on the total weight of the neutralizing conditioner. The total amount of the one or more cationic polymers may be about 0.01 to about 8 wt. %, about 0.01 to about 5 wt. %, about 0.01 to about 3 wt. %, about 0.1 to about 10 wt. %, about 0.1 to about 8 wt. %, about 0.1 to about 5 wt. %, or about 0.1 to about 3 wt. %.

According to an embodiment of the instant disclosure, methods for treating hair include:
i. applying a chemical relaxer composition to the hair and relaxing the hair, for example, a chemical relaxer composition comprising:
   a. one or more caustic agents such as sodium hydroxide:
   b. one or more fatty compounds, one or more surfactants,
   c. one or more water-soluble solvents, and/or
   d. one or more cationic polymers;
   and allowing the chemical relaxer composition to remain on the hair for a period of time sufficient to chemically relax the hair (e.g., from about 5 to about 30 min., about 5 to about 25 min., or about 10 to about 20 min.);
ii. rinsing the chemical relaxer composition from the hair, typically with water;
iii. applying a neutralizing composition to the hair within about 30, about 15, or about 5 minutes from rinsing the chemical relaxer composition from the hair, the neutralizing composition comprising:
   a. at least 0.5 to about 8 wt. %, about 1 to about 6 wt. %, or about 1 to about 5 wt. % of maleic acid and/or a salt thereof, based on the total weight of the neutralizing composition;
   b. about 0.2 to about 5 wt. %, about 0.2 to about 4 wt. %, or about 0.5 to about 3 wt. % of monoethanolamine, based on the total weight of the neutralizing composition; and
   c. about 75 to about 99 wt. %, about 85 to about 98 wt. %, or about 90 to about 98 wt. % of water;
   wherein the ratio of maleic acid and/or a salt thereof to monethanolamine in the neutralizing composition is about 1:1 to about 5:1, about 1:1 to about 1:4, or about 1:1 to about 3:1 (maleic acid:monethanolamine);
iv. allowing the neutralizing composition to remain on the hair for a period of time, for example, about 8 to about 15 min., about 8 to about 12 min., or about 10 min;
v. after the neutralizing composition has remained on the hair for the period of time, without rinsing the neutralizing composition from the hair, applying a neutralizing conditioner to the hair, the neutralizing conditioner comprising:
   a. at least 0.5 to about 8 wt. %, about 1 to about 6 wt. %, or about 1 to about 5 wt. % of maleic acid, based on the total weight of the neutralizing conditioner;
   b. about 0.2 to about 5 wt. %, about 0.2 to about 4 wt. %, or about 0.5 to about 3 wt. % of monoethanolamine, based on the total weight of the neutralizing conditioner;
   c. about 0.1 to about 10 wt. %, about 0.5 to about 5 wt. %, or about 1 to about 5 wt. % of one or more cationic surfactants, based on the total weight of the neutralizing conditioner;
   d. about 0.5 to about 20 wt. %, about 1 to about 15 wt. %, or about 1 to about 10 wt. % of one or more fatty compounds;
   e. about 0.5 to about 20 wt. %, about 1 to about 15 wt. %, or about 1 to about 10 wt. % of one or more water-soluble solvents, based on the total weight of the neutralizing conditioner; and
   f. about 50 to about 90 wt. %, about 70 to about 90 wt. %, or about 80 to about 90 wt. % of water, based on the total weight of the neutralizing conditioner;
   wherein the ratio of maleic acid to monethanolamine in the neutralizing conditioner is about 1:1 to about 5:1, about 1:1 to about 1:4, or about 1:1 to about 3:1 (maleic acid:monethanolamine);
vi. allowing the neutralizing conditioner to remain on the hair for a period of time, for example, about 8 to about 15 min., about 8 to about 12 min., or about 10 min;
vii. rinsing the neutralizing conditioner and the neutralizing composition from the hair;
viii. applying a shampoo to the hair after rinsing the neutralizing conditioner and the neutralizing composition from the hair; and
ix rinsing the shampoo from the hair.

After rinsing the neutralizing conditioner and the neutralizing composition from the hair, the hair may further shampooed with a shampoo and/or conditioned with a conditioner. Also, the hair may be subsequently dried and styled, for example, the hair may be dried with a blow dryer and/or styled with a hot iron. In another embodiment, the methods according to the disclosure include:
A. applying a chemical relaxer composition to the hair and relaxing the hair, for example, a chemical relaxer composition comprising:
   a. one or more caustic agents such as sodium hydroxide:
   b. one or more fatty compounds, one or more surfactants,
   c. one or more water-soluble solvents, and/or
   d. one or more cationic polymers;
   and allowing the chemical relaxer composition to remain on the hair for a period of time sufficient to chemically relax the hair (e.g., from about 5 to about 30 min., about 5 to about 25 min., or about 10 to about 20 min.);
B. rinsing the chemical relaxer composition from the hair;
C. applying a neutralizing composition to the hair within 15 minutes from rinsing the chemical relaxer composition from the hair, the neutralizing composition comprising:
   a. at least 0.5 to about 8 wt. % of maleic acid and/or a salt thereof, based on the total weight of the neutralizing composition;
   b. about 0.2 to about 5 wt. % of monoethanolamine, based on the total weight of the neutralizing composition; and
   c. about 85 to about 98 wt. % of water;
      wherein the ratio of maleic acid and/or a salt thereof to monethanolamine in the neutralizing composition is about 1:1 to about 3:1;
D. allowing the neutralizing composition to remain on the hair for about 10 minutes;
E. after the neutralizing composition has remained on the hair for about 10 minutes, without rinsing the neutralizing composition from the hair, applying a neutralizing conditioner to the hair, the neutralizing conditioner comprising:
   a. about 1 to about 5 wt. % of maleic acid and/or a salt thereof, based on the total weight of the neutralizing conditioner;
   b. about 0.2 to about 3 wt. % of monoethanolamine, based on the total weight of the neutralizing conditioner;
   c. about 0.5 to about 5 wt. % of one or more cationic surfactants, based on the total weight of the neutralizing conditioner;
   d. about 0.5 to about 20 wt. % of one or more fatty compounds;
   e. about 0.5 to about 20 wt. % of one or more water-soluble solvents, based on the total weight of the neutralizing conditioner; and
   f. about 60 to about 90 wt. % water, based on the total weight of the neutralizing conditioner;
      wherein the ratio of maleic acid to monethanolamine in the neutralizing conditioner is about 1:1 to about 3:1;
F. allowing the neutralizing conditioner to remain on the hair for about 10 minutes;
G. rinsing the neutralizing conditioner and the neutralizing composition from the hair;
H. applying a shampoo to the hair within 15 minutes from rinsing the neutralizing conditioner and the neutralizing composition from the hair; and
I. rinsing the shampoo from the hair.

After rinsing the neutralizing conditioner and the neutralizing composition from the hair, the hair may further shampooed with a shampoo and/or conditioned with a conditioner. Also, the hair may be subsequently dried and styled, for example, the hair may be dried with a blow dryer and/or styled with a hot iron.

The compositions used in the methods of the disclosure may be incorporated into kits. For example, the kits may include at least one neutralizing composition and at least one neutralizing conditioner, which are separately contained. The neutralizing composition may be a concentrated neutralizing conditioner, which is diluted prior to application to the hair. A concentrated neutralizing composition may be diluted with water in a ratio of about 1:1 to about 1:10 (concentrated neutralizing composition:water). The dilution ratio may also be about 1:2 to about 1:8, about 1:3 to about 1:7, about 1:4 to about 1:6, or about 1:6 (e.g., one part concentrated neutralizing composition combined with six parts of water). The kits may also include a chemical relaxing composition. In some cases, the kits may also include a shampooing and/or cleansing composition (e.g., a shampoo, a conditioner (different than the neutralizing conditioner), a conditioning shampoo (all-in-one shampoo/conditioner), etc.). Instructions, mixing components, brushes, gloves, measuring tools, etc., may also be included in the kits. In one embodiment, kits according to the instant disclosure include at least: a concentrated neutralizing composition and neutralizing shampoo, which are separately contained. Also, included are mixing instructions and/or application instructions (e.g., instructions regarding how to dilute the concentrated neutralizing composition and/or instructions regarding how to use the compositions of the kits for treating hair).

The compositions of the instant disclosure may be packaged in a variety of different containers. Non-limiting examples of useful packaging include tubes, jars, caps, unit dose packages, bottles, etc., including squeezable tubes and bottles.

The methods of the disclosure dramatically improve the quality and durability of the chemically relaxed hair. Accordingly, the disclosure relates to methods for repairing, minimizing, and/or compensating for damage to chemically relaxed hair. Moreover, the disclosure relates to methods for restructuring, strengthening, and/or rejuvenating the keratin fibers of hair. Along these lines, as shown the by testing described herein, the disclosure relates to methods for improving the Young's modulus of hair and to methods for improving the break stress of the hair. Therefore, in some instances, the methods relate to increasing the mean Young's modulus of chemically relaxed hair by at least 5%, 10%, 15%, 20%, 25%, or more, relative to chemically relaxed hair not treated according to the described methods (e.g., relative to hair treated in the same manner as hair treated according to the disclosed methods but without treatment with a neutralizing composition and a neutralizing conditioner). In some cases, the Young's modulus is increased by about 5 to about 30%, about 10 to about 30%, about 15 to about 30%, about 5 to about 25%, about 10 to about 25%, or about 15 to about 25%, relative to chemically relaxed hair not treated according to the described methods.

Likewise, in some instances, the methods relate to increasing the mean break stress of chemically relaxed hair by at least 5%, 10%, 12%, or 15%, or more, relative to chemically relaxed hair not treated according to the described methods (e.g., relative to hair treated in the same manner as hair treated according to the disclosed methods but without treatment with a neutralizing composition and a neutralizing conditioner). In some cases, the break stress is increased by about 5 to about 20%, about 10 to about 20%, or about 10 to about 15% relative to chemically relaxed hair not treated according to the described methods.

More exhaustive but non-limiting lists of components useful in the chemical relaxer compositions, the neutralizing compositions, and the neutralizing conditioners of the instant disclosure are provided below.

Cationic Surfactants

The term "cationic surfactant" means a surfactant that is positively charged when it is contained in the composition according to the disclosure. This surfactant may bear one or more positive permanent charges or may contain one or more functions that are cationizable in the composition according to the disclosure.

Non-limiting examples of cationic surfactants include behenalkonium chloride, benzethonium chloride, cetylpyridinium chloride, behentrimonium chloride, lauralkonium chloride, cetalkonium chloride, cetrimonium bromide, cetrimonium chloride, cethylamine hydrofluoride, chlorallyl-methenamine chloride (Quaternium-15), distearyldimonium chloride (Quaternium-5), dodecyl dimethyl ethylbenzyl ammonium chloride (Quaternium-14), Quaternium-22, Quaternium-26, Quaternium-18 hectorite, dimethylamino-ethylchloride hydrochloride, cysteine hydrochloride, diethanolammonium POE (10) oletyl ether phosphate, diethanolammonium POE (3)oleyl ether phosphate, tallow alkonium chloride, dimethyl dioctadecylammoniumbentonite, stearalkonium chloride, domiphen bromide, denatonium benzoate, myristalkonium chloride, laurtrimonium chloride, ethylenediamine dihydrochloride, guanidine hydrochloride, pyridoxine HCl, iofetamine hydrochloride, meglumine hydrochloride, methylbenzethonium chloride, myrtrimonium bromide, oleyltrimonium chloride, polyquaternium-1, procainehydrochloride, stearalkonium bentonite, stearalkoniumhectonite, stearyl trihydroxyethyl propylenediamine dihydrofluoride, tallowtrimonium chloride, and hexadecyltrimethyl ammonium bromide.

The cationic surfactant(s) may be chosen from optionally polyoxyalkylenated, primary, secondary or tertiary fatty amines, or salts thereof, and quaternary ammonium salts, and a mixture thereof.

The fatty amines generally comprise at least one $C_8$-$C_{30}$ hydrocarbon-based chain.

Examples of quaternary ammonium salts that may especially be mentioned include: those corresponding to the general formula (III) below:

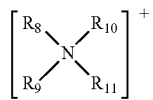
(III)

in which the groups $R_8$ to $R_{11}$, which may be identical or different, represent a linear or branched, saturated or unsaturated aliphatic group comprising from 1 to 30 carbon atoms, or an aromatic group such as aryl or alkylaryl, at least one of the groups $R_8$ to $R_{11}$ denoting a group comprising from 8 to 30 carbon atoms and preferably from 12 to 24 carbon atoms. The aliphatic groups may comprise heteroatoms especially such as oxygen, nitrogen, sulfur and halogens. The aliphatic groups are chosen, for example, from $C_1$-$C_{30}$ alkyl, $C_2$-$C_{30}$ alkenyl, $C_1$-$C_{30}$ alkoxy, polyoxy($C_2$-$C_6$)alkylene, $C_1$-$C_{30}$ alkylamide, ($C_{12}$-$C_{22}$)alkylamido($C_2$-$C_6$)alkyl, ($C_{12}$-$C_{22}$)alkyl acetate and $C_1$-$C_{30}$ hydroxyalkyl groups; X⁻ is an anion chosen from the group of halides, phosphates, acetates, lactates, ($C_1$-$C_4$)alkyl sulfates, and ($C_1$-$C_4$)alkyl- or ($C_1$-$C_4$)alkylarylsulfonates.

Among the quaternary ammonium salts of formula (III), those that are preferred are, on the one hand, tetraalkylammonium salts, for instance dialkyldimethylammonium or alkyltrimethylammonium salts in which the alkyl group contains approximately from 12 to 22 carbon atoms, in particular behenyltrimethylammonium, distearyldimethylammonium, cetyltrimethylammonium or benzyldimethylstearylammonium salts, or, on the other hand, oleocetyldimethylhydroxyethylammonium salts, palm itylam idopropyltrimethylammonium salts, stearamidopropyltrimethylammonium salts and stearamidopropyldimethylcetearylammonium salts.

In some cases it is useful to use salts such as the chloride salts of the following compounds:

A. a quaternary ammonium salt of imidazoline, such as, for example, those of formula (IV) below:

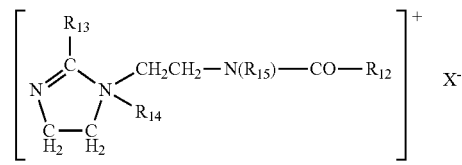
(IV)

in which $R_{12}$ represents an alkenyl or alkyl group comprising from 8 to 30 carbon atoms, derived for example from tallow fatty acids, $R_{13}$ represents a hydrogen atom, a $C_1$-$C_4$ alkyl group or an alkyl or alkenyl group comprising from 8 to 30 carbon atoms, $R_{14}$ represents a $C_1$-$C_4$ alkyl group, $R_{15}$ represents a hydrogen atom or a $C_1$-$C_4$ alkyl group, X⁻ is an anion chosen from the group of halides, phosphates, acetates, lactates, alkyl sulfates, alkyl- or alkylaryl-sulfonates in which the alkyl and aryl groups preferably comprise, respectively, from 1 to 20 carbon atoms and from 6 to 30 carbon atoms. $R_{12}$ and $R_{13}$ preferably denote a mixture of alkenyl or alkyl groups containing from 12 to 21 carbon atoms, derived for example from tallow fatty acids, $R_{14}$ preferably denotes a methyl group, and $R_{15}$ preferably denotes a hydrogen atom. Such a product is sold, for example, under the name REWOQUAT W 75 by the company Evonik;

B. a quaternary diammonium or triammonium salt, in particular of formula (V):

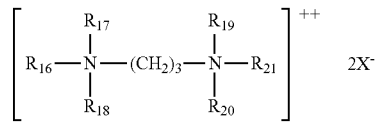
(V)

in which $R_{16}$ denotes an alkyl radical comprising approximately from 16 to 30 carbon atoms, which is optionally hydroxylated and/or interrupted with one or more oxygen atoms, $R_{17}$ is chosen from hydrogen or an alkyl radical comprising from 1 to 4 carbon atoms or a group ($R_{16a}$)($R_{17a}$)($R_{18a}$)N—(CH$_2$)$_3$, $R_{16a}$, $R_{17a}$, $R_{18a}$, $R_{18}$, $R_{19}$, $R_{20}$ and $R_{21}$, which may be identical or different, being chosen from hydrogen and an alkyl radical comprising from 1 to 4 carbon atoms, and X⁻ is an anion chosen from the group of halides, acetates, phosphates, nitrates and methyl sulfates. Such compounds are, for example, FINQUAT CT-P, sold by the company Innospec (Quaternium 89), and FINQUAT CT, sold by the company Innospec (Quaternium 75), C. a quaternary ammonium salt containing at least one ester function, such as those of formula (VI) below:

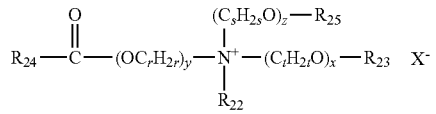
(VI)

in which:

$R_{22}$ is chosen from $C_1$-$C_6$ alkyl groups and $C_1$-$C_6$ hydroxyalkyl or dihydroxyalkyl groups;

$R_{23}$ is chosen from:

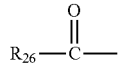

$R_{27}$, which is a linear or branched, saturated or unsaturated $C_1$-$C_{22}$ hydrocarbon-based group, and a hydrogen atom, $R_{25}$ is chosen from:

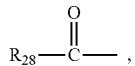

$R_{29}$, which is a linear or branched, saturated or unsaturated $C_1$-$C_6$ hydrocarbon-based group, and a hydrogen atom, $R_{24}$, $R_{26}$ and $R_{28}$, which may be identical or different, are chosen from linear or branched, saturated or unsaturated $C_7$-$C_{21}$ hydrocarbon-based groups;

r, s and t, which may be identical or different, are integers ranging from 2 to 6;

y is an integer ranging from 1 to 10;

x and z, which may be identical or different, are integers ranging from 0 to 10;

$X^-$ is a simple or complex, organic or mineral anion;

with the proviso that the sum x+y+z is from 1 to 15, that when x is 0 then $R_n$ denotes $R_{27}$, and that when z is 0 then $R_{25}$ denotes $R_{29}$.

The alkyl groups $R_{22}$ may be linear or branched, and more particularly linear. In some cases, $R_{22}$ denotes a methyl, ethyl, hydroxyethyl or dihydroxypropyl group, and more particularly a methyl or ethyl group. Advantageously, the sum x+y+z is from 1 to 10.

When $R_{23}$ is a hydrocarbon-based group $R_{27}$, it may be long and contain from 12 to 22 carbon atoms, or may be short and contain from 1 to 3 carbon atoms. When $R_{25}$ is an $R_{29}$ hydrocarbon-based group, it preferably contains 1 to 3 carbon atoms. Advantageously, $R_{24}$, $R_{26}$ and $R_{28}$, which may be identical or different, are chosen from linear or branched, saturated or unsaturated $C_{11}$-$C_{21}$ hydrocarbon-based groups, and more particularly from linear or branched, saturated or unsaturated $C_{11}$-$C_{21}$ alkyl and alkenyl groups.

In some cases, x and z, which may be identical or different, have values of 0 or 1. Likewise, in some cases y is equal to 1. In some cases, r, s and t, which may be identical or different, are equal to 2 or 3, and even more particularly are equal to 2.

The anion $X^-$ is may be a halide (chloride, bromide or iodide) or an alkyl sulfate, more particularly methyl sulfate. However, use may be made of methanesulfonate, phosphate, nitrate, tosylate, an anion derived from an organic acid, such as acetate or lactate, or any other anion compatible with the ammonium containing an ester function.

The anion $X^+$ is even more particularly chloride or methyl sulfate.

Use is made more particularly, in the composition according to the invention, of the ammonium salts of formula (VI) in which:

$R_{22}$ denotes a methyl or ethyl group, x and y are equal to 1;

z is equal to 0 or 1;

r, s and t are equal to 2;

$R_{23}$ is chosen from:

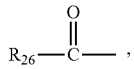

methyl, ethyl or $C_{14}$-$C_{22}$ hydrocarbon-based groups, and a hydrogen atom;

$R_{25}$ is chosen from:

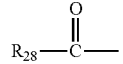

and a hydrogen atom;

$R_{24}$, $R_{26}$ and $R_{28}$, which may be identical or different, are chosen from linear or branched, saturated or unsaturated $C_{13}$-$C_{17}$ hydrocarbon-based groups, and preferably from linear or branched, saturated or unsaturated $C_{13}$-$C_{17}$ alkyl and alkenyl groups. The hydrocarbon-based groups are advantageously linear.

Mention may be made, for example, of the compounds of formula (VI) such as the diacyloxyethyldimethylammonium, diacylo xyethylhydroxyethylmethylammonium, monoacyloxyethyldihydroxyethylmethylammonium, triacyloxyethylmethylammonium and monoacyloxyethylhydroxyethyldimethylammonium salts (chloride or methyl sulfate in particular), and a mixture thereof. The acyl groups preferably contain 14 to 18 carbon atoms and are obtained more particularly from a plant oil, such as palm oil or sunflower oil. When the compound contains several acyl groups, these groups may be identical or different.

These products are obtained, for example, by direct esterification of triethanolamine, triisopropanolamine, an alkyldiethanolamine or an alkyldiisopropanolamine, which are optionally oxyalkylenated, with $C_{10}$-$C_{30}$ fatty acids or with mixtures of $C_{10}$-$C_{30}$ fatty acids of plant or animal origin, or by transesterification of the methyl esters thereof. This esterification is followed by quaternization using an alkylating agent such as an alkyl (preferably methyl or ethyl) halide, a dialkyl (preferably methyl or ethyl) sulfate, methyl methanesulfonate, methyl para-toluenesulfonate, glycol chlorohydrin or glycerol chlorohydrin. Such compounds are, for example, sold under the names DEHYQUART by the company BASF, STEPANQUAT by the company Stepan, NOXAMIUM by the company Ceca or REWOQUAT WE 18 by the company Evonik.

Water-Soluble Solvents

The term "water-soluble solvent" is interchangeable with the term "water-miscible solvent" and means a compound that is liquid at 25° C. and at atmospheric pressure (760 mmHg), and it has a solubility of at least 50% in water under these conditions. The hair-treatment compositions of the instant disclosure may include one or more water-soluble solvents.

Water-soluble solvents include, for example, glycerin, $C_{1-4}$ alcohols, organic solvents, fatty alcohols, fatty ethers, fatty esters, polyols, glycols, vegetable oils, mineral oils, liposomes, laminar lipid materials, or any a mixture thereof. As examples of organic solvents, non-limiting mentions can be made of monoalcohols and polyols such as ethyl alcohol, isopropyl alcohol, propyl alcohol, benzyl alcohol, and phenylethyl alcohol, or glycols or glycol ethers such as, for example, monomethyl, monoethyl and monobutyl ethers of ethylene glycol, propylene glycol or ethers thereof such as, for example, monomethyl ether of propylene glycol, butylene glycol, hexylene glycol, dipropylene glycol as well as alkyl ethers of diethylene glycol, for example monoethyl ether or monobutyl ether of diethylene glycol. Other suitable examples of organic solvents are ethylene glycol, propylene glycol, butylene glycol, hexylene glycol, propane diol, and glycerin. The organic solvents can be volatile or non-volatile compounds.

Further non-limiting examples of water-soluble solvents which may be used include alkanediols (polyhydric alcohols) such as glycerin, 1,2,6-hexanetriol, trimethylolpropane, ethylene glycol, propylene glycol, diethylene glycol, triethylene glycol, tetraethylene glycol, pentaethylene glycol, dipropylene glycol, 2-butene-1,4-diol, 2-ethyl-1,3-hexanediol, 2-methyl-2,4-pentanediol, (caprylyl glycol), 1,2-hexanediol, 1,2-pentanediol, and 4-methyl-1,2-pentanediol; alkyl alcohols having 1 to 4 carbon atoms such as ethanol, methanol, butanol, propanol, and isopropanol; glycol ethers such as ethylene glycol monomethyl ether, ethylene glycol monoethyl ether, ethylene glycol monobutyl ether, ethylene glycol monomethyl ether acetate, diethylene glycol monomethyl ether, diethylene glycol monoethyl ether, diethylene glycol mono-n-propyl ether, ethylene glycol mono-iso-propyl ether, diethylene glycol mono-iso-propyl ether, ethylene glycol mono-n-butyl ether, ethylene glycol mono-t-butyl ether, diethylene glycol mono-t-butyl ether, 1-methyl-1-methoxybutanol, propylene glycol monomethyl ether, propylene glycol monoethyl ether, propylene glycol mono-t-butyl ether, propylene glycol mono-n-propyl ether, propylene glycol mono-iso-propyl ether, dipropylene glycol monomethyl ether, dipropylene glycol monoethyl ether, dipropylene glycol mono-n-propyl ether, and dipropylene glycol mono-iso-propyl ether; 2-pyrrolidone, N-methyl-2-pyrrolidone, 1,3-dimethyl-2-imidazolidinone, formamide, acetamide, dimethyl sulfoxide, sorbit, sorbitan, acetine, diacetine, triacetine, sulfolane, and a mixture thereof.

In some cases, the water-soluble solvent may be selected from the group consisting of one or more glycols, $C_{1-4}$ alcohols, glycerin, and a mixture thereof. In some cases, the water-soluble solvent is selected from the group consisting of hexylene glycol, proplene glycol, caprylyl glycol, glycerin, isopropyl alcohol, and a mixture thereof.

Polyhydric alcohols are useful. Examples of polyhydric alcohols include glycerin, ethylene glycol, diethylene glycol, triethylene glycol, propylene glycol, dipropylene glycol, tripropylene glycol, 1,3-butanediol, 2,3-butanediol, 1,4-butanediol, 3-methyl-1,3-butanediol, 1,5-pentanediol, tetraethylene glycol, 1,6-hexanediol, 2-methyl-2,4-pentanediol, polyethylene glycol, 1,2,4-butanetriol, 1,2,6-hexanetriol, and a mixture thereof.

Polyol compounds may also be used. Non-limiting examples include the aliphatic diols, such as 2-ethyl-2-methyl-1,3-propanediol, 3,3-dimethyl-1,2-butanediol, 2,2-diethyl-1,3-propanediol, 2-methyl-2-propyl-1,3-propanediol, 2,4-dimethyl-2,4-pentanediol, 2,5-dimethyl-2,5-hexanediol, 5-hexene-1,2-diol, and 2-ethyl-1,3-hexanediol, and a mixture thereof.

Fatty Compounds

Non-limiting examples of fatty compounds include oils, mineral oil, fatty alcohols, fatty acids, fatty alcohol derivatives, fatty acid derivatives (such as alkoxylated fatty acids or polyethylene glycol esters of fatty acids or propylene glycol esters of fatty acids or butylene glycol esters of fatty acids or esters of neopentyl glycol and fatty acids or polyglycerol/glycerol esters of fatty acids or glycol diesters or diesters of ethylene glycol and fatty acids or esters of fatty acids and fatty alcohols, esters of short chain alcohols and fatty acids), esters of fatty alcohols, hydroxy-substituted fatty acids, waxes, triglyceride compounds, lanolin, and a mixture thereof. For instance, one or more fatty compounds may be selected from the group consisting of glycol distearate, PEG-55 propylene glycol oleate, cetearyl alcohol, soybean oil, cetyl esters, isononanoate isopropyl myristate, cetearyl alcohol, orbigynya oleifera seed oil, propylene glycol dicaprylate/dicaprate, mineral oil, and a mixture thereof.

Non-limiting examples of the fatty alcohols, fatty acids, fatty alcohol derivatives, and fatty acid derivatives are found in International Cosmetic Ingredient Dictionary, Sixteenth Edition, 2016, which is incorporated by reference herein in its entirety.

Fatty alcohols useful herein include those having from about 10 to about 30 carbon atoms, from about 12 to about 22 carbon atoms, and from about 16 to about 22 carbon atoms. These fatty alcohols can be straight or branched chain alcohols and can be saturated or unsaturated. Nonlimiting examples of fatty alcohols include decyl alcohol, undecyl alcohol, dodecyl, myristyl, cetyl alcohol, stearyl alcohol, isostearyl alcohol, isocetyl alcohol, behenyl alcohol, linalool, oleyl alcohol, cholesterol, cis4-t-butylcyclohexanol, myricyl alcohol and a mixture thereof. In some cases, the fatty alcohols are those selected from the group consisting of cetyl alcohol, stearyl alcohol, isostearyl alcohol, oleyl alcohol, and a mixture thereof.

Fatty acids useful herein include those having from about 10 to about 30 carbon atoms, from about 12 to about 22 carbon atoms, and from about 16 to about 22 carbon atoms. These fatty acids can be straight or branched chain acids and can be saturated or unsaturated. Also included are diacids, triacids, and other multiple acids which meet the carbon number requirement herein. Also included herein are salts of these fatty acids. Nonlimiting examples of fatty acids include lauric acid, palmitic acid, stearic acid, behenic acid, arichidonic acid, oleic acid, isostearic acid, sebacic acid, and a mixture thereof. In some cases, the fatty acids are selected from the group consisting of palmitic acid, stearic acid, and a mixture thereof.

Fatty alcohol derivatives include alkyl ethers of fatty alcohols, alkoxylated fatty alcohols, alkyl ethers of alkoxylated fatty alcohols, esters of fatty alcohols and a mixture thereof. Nonlimiting examples of fatty alcohol derivatives include materials such as methyl stearyl ether; 2-ethylhexyl dodecyl ether; stearyl acetate; cetyl propionate; the ceteth series of compounds such as ceteth-1 through ceteth-45, which are ethylene glycol ethers of cetyl alcohol, wherein the numeric designation indicates the number of ethylene glycol moieties present; the steareth series of compounds such as steareth-1 through 10, which are ethylene glycol ethers of steareth alcohol, wherein the numeric designation indicates the number of ethylene glycol moieties present; ceteareth 1 through ceteareth-10, which are the ethylene glycol ethers of ceteareth alcohol, i.e. a mixture of fatty alcohols containing predominantly cetyl and stearyl alcohol, wherein the numeric designation indicates the number of ethylene glycol moieties present; C1-C30 alkyl ethers of the ceteth, steareth, and ceteareth compounds just described; polyoxyethylene ethers of branched alcohols such as octyldodecyl alcohol, dodecylpentadecyl alcohol, hexyldecyl alcohol, and isostearyl alcohol; polyoxyethylene ethers of behenyl alcohol; PPG ethers such as PPG-9-steareth-3, PPG-11 stearyl ether, PPG8-ceteth-1, and PPG-10 cetyl ether; and a mixture thereof.

Non-limiting olyglycerol esters of fatty acids include those of the following formula:

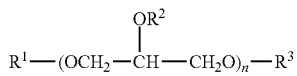

wherein the average value of n is about 3 and $R^1$, $R^2$ and $R^3$ each may independently be a fatty acid moiety or hydrogen, provided that at least one of $R^1$, $R^2$, and $R^3$ is a fatty acid moiety. For instance, $R^1$, $R^2$ and $R^3$ may be saturated or unsaturated, straight or branched, and have a length of $C_1$-$C_{40}$, $C_1$-$C_{30}$, $C_1$-$C_{25}$, or $C_1$-$C_{20}$, $C_1$-$C_{16}$, or $C_1$-$C_{10}$. For example, nonionic polyglycerol esters of fatty acids include polyglyceryl-5 laurate, The fatty acid derivatives are defined herein to include fatty acid esters of the fatty alcohols as defined above, fatty acid esters of the fatty alcohol derivatives as defined above when such fatty alcohol derivatives have an esterifiable hydroxyl group, fatty acid esters of alcohols other than the fatty alcohols and the fatty alcohol derivatives described above, hydroxy-substituted fatty acids, and a mixture thereof. Nonlimiting examples of fatty acid derivatives include ricinoleic acid, glycerol monostearate, 12-hydroxy stearic acid, ethyl stearate, cetyl stearate, cetyl palmitate, polyoxyethylene cetyl ether stearate, polyoxyethylene stearyl ether stearate, polyoxyethylene lauryl ether stearate, ethyleneglycol monostearate, polyoxyethylene monostearate, polyoxyethylene distearate, propyleneglycol monostearate, propyleneglycol distearate, trimethylolpropane distearate, sorbitan stearate, polyglyceryl stearate, dimethyl sebacate, PEG-15 cocoate, PPG-15 stearate, glyceryl monostearate, glyceryl distearate, glyceryl tristearate, PEG-8 laurate, PPG-2 isostearate, PPG-9 laurate, and a mixture thereof. Preferred for use herein are glycerol monostearate, 12-hydroxy stearic acid, and a mixture thereof.

In some cases, the one or more fatty compounds may be one or more high melting point fatty compounds. A high melting point fatty compound is a fatty compound having a melting point of 25° C. Even higher melting point fatty compounds may also be used, for example, fatty compounds having a melting point of 40° C. or higher, 45° C. or higher, 50° C. or higher. The high melting point fatty compound may be selected from the group consisting of fatty alcohols, fatty acids, fatty alcohol derivatives, fatty acid derivatives, and mixtures thereof. Nonlimiting examples of the high melting point compounds are found in International Cosmetic Ingredient Dictionary, Fifteenth Edition, 2014, which is incorporated herein by reference in its entirety. The fatty alcohols useful herein are those having from about 14 to about 30 carbon atoms, preferably from about 16 to about 22 carbon atoms. These fatty alcohols are saturated and can be straight or branched chain alcohols. Non-limiting examples of high melting point fatty compounds include fatty alcohols such as, for example, cetyl alcohol (having a melting point of about 56° C.), stearyl alcohol (having a melting point of about 58-59° C.), behenyl alcohol (having a melting point of about 71° C.), and mixtures thereof. These compounds are known to have the above melting point. However, they often have lower melting points when supplied, since such supplied products are often mixtures of fatty alcohols having alkyl chain length distribution in which the main alkyl chain is cetyl, stearyl or behenyl group. In the present application, more preferred fatty alcohols are cetyl alcohol, stearyl alcohol and mixtures thereof.

Thickening Agents

Thickening agents (also referred to as thickeners or viscosity modifying agents) are well known. Classes of such agents include, but are not limited to, semisynthetic polymers, such as semisynthetic cellulose derivatives, synthetic polymers, such as carbomers, poloxamers, and acrylates/beheneth-25 methacrylate copolymer, acrylates copolymer, polyethyleneimines (e.g., PEI-10), naturally occurring polymers, such as acacia, tragacanth, alginates (e.g., sodium alginate), carrageenan, vegetable gums, such as xanthan gum, petroleum jelly, waxes, particulate associate colloids, such as bentonite, colloidal silicon dioxide, and microcrystalline cellulose, surfactants, such as PPG-2 hydroxyethyl coco/isostearamide, emulsifiers, such as distearth-75 IPDI, and salts, such as sodium chloride, starches, such as hydroxypropyl starch phosphate, potato starch (modified or unmodified), celluloses such as hydroxyethylcellulose, guars such as hydroxypropyl guar, and a mixture thereof.

In some cases, the thickening agents may include one or more associative thickening polymers such as anionic associative polymers, amphoteric associative polymers, cationic associative polymers, nonionic associative polymers, and a mixture thereof. A non-limiting example of an amphoteric associative polymer is acrylates/beheneth-25methacrylate copolymer, sold under the tradename NOVETHIX L-10 (Lubrizol). Non-limiting examples of anionic associative polymers include INCI name: acrylates copolymer, sold under the tradename CARBOPOL Aqua SF-1 (Lubrizol), INCI name: acrylates crosspolymer-4, sold under the tradename CARBOPOL Aqua SF-2 (Lubrizol), and a mixture thereof. The associative thickening polymers, for instance, the acrylates copolymer and/or the acrylates crosspolymer-4, may be neutralized in water or an aqueous solution with a neutralizing agent before the polymer is added into a hair-treatment composition.

Cationic Polymers poly(methacryloyloxyethyl trimethylammonium chloride), polyquaternium-37, quaternized cellulose derivatives, polyquaternium-4, polyquaternium-10, cationic alkyl polyglycosides, cationized honey, cationic guar derivatives, polymeric dimethyl diallyl ammonium salts and copolymers thereof with esters and amides of acrylic acid and methacrylic acid, copolymers of vinyl pyrrolidone with quaternized derivatives of dialkylaminoalkyl acrylate and methacrylate, vinyl pyrrolidone-vinyl imidazolium methochloride copolymers, quaternized polyvinyl alcohol, polyquaternium-2, polyquaternium-7, polyquaternium-17, polyquaternium-18, polyquaternium-24, polyquaternium-27, and a mixture thereof. In some instances, the one or more cationic polymers may be selected from the group consisting of polyquaternium-4, polyquaternium-10, cationic guar derivatives, and a mixture thereof.

The cationic polymers can be a monoalkyl quaternary amine, such as stearyltrimonium chloride, soyatrimonium chloride or coco-ethyldimonium ethosulfate. Other suitable cationic polymers include, but are not limited to, behentrimonium chloride, dialkyl quaternary amines, such as dicetyldimonium chloride, dicocodimethyl ammonium chloride or distearyldimethyl ammonium chloride; and polyquaternium compounds, such as Polyquaternium-6, Polyquaternium-22 or Polyquaternium-5.

For example, cationic polymers may be chosen from

In some instances, the cationic polymers are cationic conditioning polymers. Examples of cationic conditioning polymers that can be used include, without limitation, cationic cellulose, cationic proteins, and cationic polymers. The cationic polymers can have a vinyl group backbone of amino and/or quaternary ammonium monomers. Cationic amino and quaternary ammonium monomers include, without limitation, dialkylamino alkylmethacrylate, monoalkylaminoalkyl acrylate, monoalkylaminoalkyl methacrylate, trialkyl methacryoloxyalkyl ammonium salt, trialkyl acryloxyalkyl ammonium salts, diallyl quaternary ammonium salts, vinyl compounds substituted with dialkyl aminoalkyl acrylate, and vinyl quaternary ammonium monomers having cyclic cationic nitrogen containing rings such as pyridinium, imidazolium, or quaternized pyrrolidine. Other examples of cationic conditioning polymers that can be used include, without limitation, hydroxypropyltrimonium honey, cocodimonium silk amino acids, cocodimonium hydroxypropyl hydrolyzed wheat or silk protein, polyquaternium-5, polyquaternium-11, polyquaternium-2, polyquaternium-4, polyquaternium-6, polyquaternium-7, polyquaternium-14, polyquaternium-16, polyquaternium-22, polyquaternium-10, and guar hydroxypropyltrimonium chloride.

In some cases quaternized polymeric cationic polymers are particularly useful. Particularly preferred are quaternary nitrogen polymers prepared by the polymerization of a dialkyldiallylammonium salt or copolymer thereof in which the alkyl group contains 1 to about 18 carbon atoms, and more preferably where the alkyl group is methyl or ethyl. Details concerning the preparation of these polymers can be found in U.S. Pat. Nos. 3,288,770, 3,412,019 and 4,772,462, incorporated herein by reference. For example, cationic homopolymers and copolymers of polydiallyldimethylammonium chloride are available in aqueous compositions sold under the trademark MERQUAT by the Calgon Corporation, subsidiary of Merck & Co., Pittsburgh, Pa. The homopolymer, which is named Polyquaternium-6 is sold under the trademark MERQUAT-100, and is described as having a weight average molecular weight of approximately 100,000. A copolymer reaction product of dimethyldiallylammonium chloride with acrylamide monomers is named Polyquaternium-7 is described as having a weight average molecular weight of approximately 500,000 and is sold under the trademark MERQUAT-550. Another copolymer reaction product of dimethyldiallylammonium chloride with acrylic acids having a weight average molecular weight from about 50,000 to about 10,000,000 has the name Polyquaternium-22 and is sold under the trademark MERQUAT-280. Polyquaternium-6 is particularly preferred.

Other polymeric conditioners include cationic copolymers of methylvinylimidazolium chloride and vinyl pyrrolidone, sold commercially by BASF Aktiengesellschaft, West Germany under the trademark LUVIQUAT at three comonomer ratios, namely at ratios of 95/5, 50/50 and 30/70 methylvinylimidazolium chloride to polyvinylpyrrolidone. These copolymers at all three comonomer ratios have the name Polyquaternium 16. Polymeric conditioners also include cationic cellulosic polymers of hydroxyethyl cellulose reacted with epichlorohydrin and quaternized with trimethylamine, sold under the trademark POLYMER JR in various viscosity grades and molecular sizes by Union Carbide Corporation, Danbury, Conn. These series of polymers are named Polyquaternium 10. Also useful are quaternized copolymers of hydroxyethylcellulose and dimethyldimethylammonium chloride, having the name Polyquaternium-4, sold in varying molecular weights under the trademark CELQUAT by National Starch and Chemical Corporation, Bridgewater, N.J.

Smaller molecule cationic non-polymeric conditioning agents can also be utilized herein. Exemplary small-molecule conditioning agents can include monofunctional or difunctional quaternary ammonium compounds, such as stearyldimethylbenzylammonium chloride, dimethyldi-(hydrogenated tallow)ammonium chloride, and the like. Non-polymeric conditioning agents can also include the quaternary ammonium salts of gluconamide derivatives, such as gamma-gluconamidopropyldimethyl-2-hydroxyethyl-ammonium chloride and minkamidopropyldimethyl-2-hydroxyethylammonium chloride identified respectively by the names Quaternium 22 and Quaternium 26. Details for the preparation of these materials are found in U.S. Pat. Nos. 3,766,267 and 4,012,398, respectively, and the materials are sold under the trademark CERAPHYL by Van Dyk & Co., Belleville, N.J. Also useful are bis-quaternary ammonium compounds which are dimers, such as 2-hydroxy propylene-bis-1,3-(dimethylstearyl ammonium chloride, designated the name, Hydroxypropyl Bisstearyldimonium chloride. The preparation of these and other bis-quat materials is described in U.S. Pat. No. 4,734,277, and such materials are sold under the trademark JORDAQUAT DIMER by Jordan Chemical Company, Folcroft, Pa.

Exemplary unquaternized polymers having tertiary amino nitrogen groups that become quaternized when protonated can include water-soluble proteinaceous quaternary ammonium compounds. Cocodimonium hydrolyzed animal protein, for example, is the name for a chemically-modified quaternary ammonium derivative of hydrolyzed collagen protein having from about 12 to about 18 carbons in at least one aliphatic alkyl group, a weight average molecular weight from about 2500 to about 12,000, and an isoionic point in a range from about 9.5 to about 11.5. This material and structurally related materials are sold under the trademarks CROQUAT and CROTEIN by Croda, Inc., New York, N.Y.

Implementation of the present disclosure is provided by way of the following examples. The examples serve to illustrate the technology without being limiting in nature.

Example 1

Concentrated Neutralizing Composition

|  | INCI US Name | wt. % |
|---|---|---|
| Active | MALEIC ACID | 10.7 |
| Active | MONOETHANOLAMINE | 5.4 |
| Water | WATER | 83.9 |

Example 2

Neutralizing Conditioner

|  | INCI US | wt. % |
|---|---|---|
| Active | MALEIC ACID | 1.9 |
| Active | ETHANOLAMINE | 0.6 |
| Cationic Surfactant(s) | BEHENTRIMONIUM METHOSULFATE, CETRIMONIUM CHLORIDE, CETRIMONIUM METHOSULFATE, STEARAMIDOPROPYL DIMETHYLAMINE, AND/OR QUATERNIUM-91 | 1.9 |
| Fatty Compound(s) | CETEARYL ALCOHOL AND/OR MINERAL OIL | 4.3 |
| Water-Soluble Solvent | GLYCERIN AND/OR PROPYLENE GLYCOL | 3.5 |

-continued

| | INCI US | wt. % |
|---|---|---|
| Cationic Polymer | POLYQUATERNIUM-37 | 0.2 |
| Thickener | HYDROXYPROPYL CELLULOSE | 0.5 |
| pH Modifier(s) | OPTIONAL COMPONENT | 0-2 |
| Preservative(s) | OPTIONAL COMPONENT | 0-2 |
| Fragrance(s) | OPTIONAL COMPONENT | 0-2 |
| Water | WATER | Q.S. |

Example 3

Testing

The mechanical properties of hair are a direct consequence of its composite structure. Accordingly, changes in mechanical properties reflect alterations in composite structure. A conventional approach for assessing mechanical properties of hair is generating a stress-strain curve by performing constant rate extension experiments. A variety of parameters can be extracted from such curves that provide information about different portions of the hair structure. A typical stress-strain curve for dry hair is provided in FIG. 1. An industry standard for generating stress-strain curves is the use of a Dia-Stron Mini Tensile Tester (MTT). Tensile testing extends fibers 100% until break at a rate of 40 mm/min. Data generated from this testing is used to assess properties of the hair structure.

Tensile testing was carried out to determine the influence of various treatments to hair, including treatments according to the methods of the instant disclosure. Testing was performed in the wet state after equilibration of hair fibers at 60% relative humidity. 50 individual fibers were prepared and tested per sample to ensure statistical rigor. Box and whisker plots were generated using Statistica™, while JMP™ analytical software was used for statistical calculations (student's t-test at 95% confidence level). All testing was performed on hair procured from International Hair Importers & Products (Glendale, N.Y.). The hair samples were mixed race hair tresses and were approximately 3 g in weight, 8" in length, and 1" wide.

Hair tresses were treated according to one of the following three protocols, A1, A2, and A3.
  A1. A sodium hydroxide based chemical relaxer composition was applied to the hair swatches and allowed to process for 20 minutes. After processing for 20 minutes, the chemical relaxer composition was rinsed from the hair swatches. The hair swatches were then shampooed and evaluated.
  A2. A sodium hydroxide based chemical relaxer composition was applied to hair swatches and allowed to process for 20 minutes. After processing for 20 minutes, the chemical relaxer composition was rinsed from the hair swatches. The hair swatches were then treated with Olaplex® Step No. 1 Bond Multiplier®, which was diluted with water (1 part of Olaplex® Step No. 1 Bond Multiplier® was combined with 6 parts water). The Olaplex® Step No. 1 Bond Multiplier® was allowed to process for 10 minutes. Without rinsing the Olaplex® Step No. 1 Bond Multiplier® from the hair, Olaplex® Bond Perfector® No. 2 was applied to the hair (Olaplex® Bond Perfector® No. 2 was layered on top of the Olaplex® Step No. 1 Bond Multiplier® that was already on the hair). Then, the Olaplex® Bond Perfector® No. 2 was allowed to remain on the hair for 10 minutes. After 10 minutes, the Olaplex® Bond Perfector® No. 2 and the underlying Olaplex® Step No. 1 Bond Multiplier® were rinsed from the hair. After rinsing, the hair swatches were shampooed and evaluated.
  A3. A sodium hydroxide based chemical relaxer composition was applied to the hair swatches and allowed to process for 20 minutes. After processing for 20 minutes, the chemical relaxer composition was rinsed from the hair swatches. The hair swatches were then treated with the Neutralizing Composition of Example 1, which was diluted with water (1 part of Neutralizing Composition of Example 1 was combined with 6 parts water). The Neutralizing Composition of Example 1 was allowed to process for 10 minutes. Without rinsing the Neutralizing Composition of Example 1 from the hair, the Neutralizing Conditioner of Example 2 was applied to the hair (Neutralizing Conditioner of Example 2 was layered on top of the Neutralizing Composition of Example 1 that was already on the hair). Then, the Neutralizing Conditioner of Example 2 was allowed to remain on the hair for 10 minutes. After 10 minutes, the Neutralizing Conditioner of Example 2 and the underlying Neutralizing Composition of Example 1 were rinsed from the hair. After rinsing, the hair swatches were shampooed and evaluated.

Hair tresses were also treated according to one of the following three protocols, B1, B2, and B3, which are similar to A1, A2, and A3, except that a guanidine relaxer composition was used to relax the hair, and the hair was conditioned after shampooing, before evaluation.
  B1. A guanidine based relaxer composition was applied to the hair swatches and allowed to process for 20 minutes. After processing for 20 minutes, the chemical relaxer composition was rinsed from the hair swatches. The hair swatches were then shampooed, conditioned, and evaluated.
  B2. A guanidine based relaxer composition was applied to hair swatches and allowed to process for 20 minutes. After processing for 20 minutes, the chemical relaxer composition was rinsed from the hair swatches. The hair swatches were then treated with Olaplex® Step No. 1 Bond Multiplier®, which was diluted with water (1 part of Olaplex® Step No. 1 Bond Multiplier® was combined with 6 parts water). The Olaplex® Step No. 1 Bond Multiplier® was allowed to process for 10 minutes. Without rinsing the Olaplex® Step No. 1 Bond Multiplier® from the hair, Olaplex® Bond Perfector® No. 2 was applied to the hair (Olaplex® Bond Perfector® No. 2 was layered on top of the Olaplex® Step No. 1 Bond Multiplier® that was already on the hair). Then, the Olaplex® Bond Perfector® No. 2 was allowed to remain on the hair for 10 minutes. After 10 minutes, the Olaplex® Bond Perfector® No. 2 and the underlying Olaplex® Step No. 1 Bond Multiplier® were rinsed from the hair. After rinsing, the hair swatches were shampooed, conditioned, and evaluated.
  B3. A guanidine based relaxer composition was applied to the hair swatches and allowed to process for 20 minutes. After processing for 20 minutes, the chemical relaxer composition was rinsed from the hair swatches. The hair swatches were then treated with the Neutralizing Composition of Example 1, which was diluted with water (1 part of Neutralizing Composition of Example 1 was combined with 6 parts water). The Neutralizing Composition of Example 1 was allowed to process for 10 minutes. Without rinsing the Neutralizing Composition of Example 1 from the hair, the Neutralizing Conditioner of Example 2 was applied to the hair (Neutralizing Conditioner of Example 2 was layered on top of the Neutralizing Composition of Example 1 that was already on the hair). Then, the Neutralizing Conditioner of Example 2 was allowed to remain on the hair for 10 minutes. After 10 minutes, the Neutralizing Conditioner of Example 2 and the underlying Neutralizing Composition of Example 1 were rinsed from the hair. After rinsing, the hair swatches were shampooed, conditioned, and evaluated.

The protocols outlined above are summarized in the table below.

| | Sodium Relaxer | Treatment 1 | Treatment 2 | Shampoo | Condition |
|---|---|---|---|---|---|
| A1 | 20 min. Rinse | Conditioner 3 min. Rinse | – | 1× | – |
| A2 | 20 min. Rinse | Olaplex ® #1 (diluted in water 1:6) 10 min. No Rinse | Olaplex ® #2 10 minutes Rinse | 1× | – |
| A3 | 20 min. Rinse | Neutralizing Composition of Ex. 1 (diluted in water 1:6) 10 min. No Rinse | Neutralizing Conditioner of Ex. 2 10 min. Rinse | 1× | – |

| | Guanidine Relaxer | Treatment 1 | Treatment 2 | Shampoo | Condition |
|---|---|---|---|---|---|
| B1 | 20 min. Rinse | Conditioner 3 min. Rinse | – | 1× | 1× |
| B2 | 20 min. Rinse | Olaplex ® #1 (diluted in water 1:6) 10 min. No Rinse | Olaplex ® #2 10 minutes Rinse | 1× | 1× |
| B3 | 20 min. Rinse | Neutralizing Composition of Ex. 1 (diluted in water 1:6) 10 min. No Rinse | Neutralizing Conditioner of Ex. 2 10 min. Rinse | 1× | 1× |

Elastic Modulus Testing (Young's Modulus)

Figure 2A:
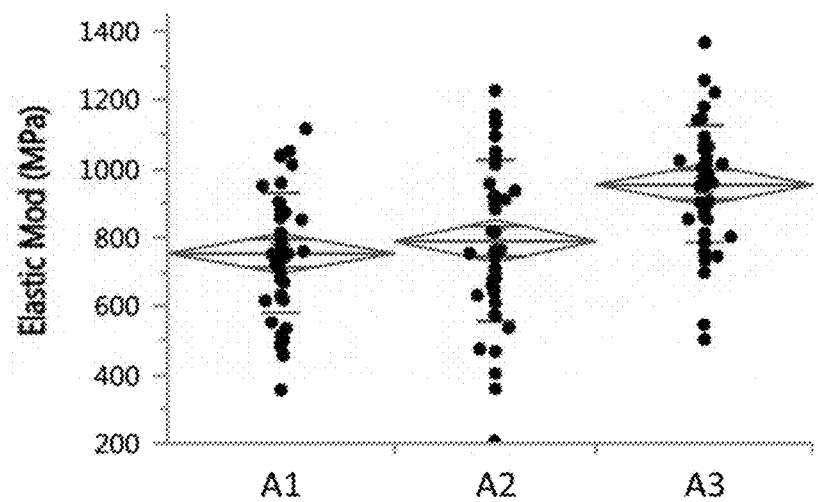
FIG. 2(a) is a graph showing the Young's modulus (the elastic modulus) of hair treated with only a sodium hydroxide based chemical relaxer composition (A1), hair treated according to a commercially available method (A2), and hair treated according to the instant disclosure (A3)
Figure 2B:
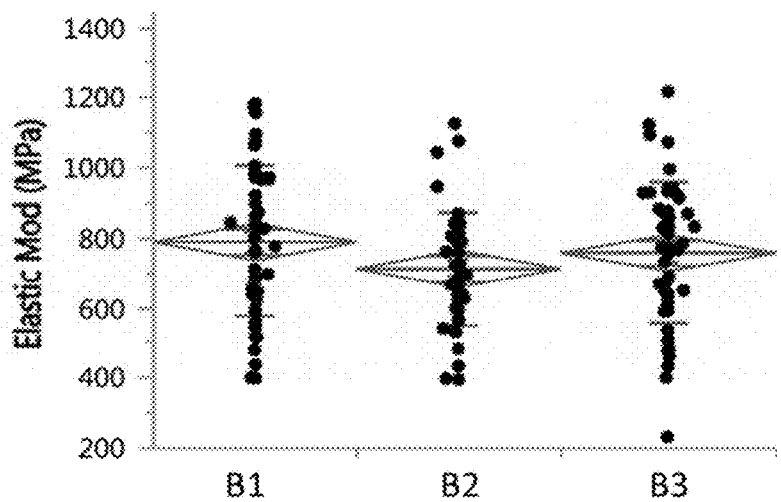
FIG. 2(b) is a graph showing the Young's modulus (the elastic modulus) of hair treated with only a guanidine based chemical relaxer composition (B1), hair treated according to a commercially available method (B2), and hair treated according to the instant disclosure (b3)

The slope of the initial portion of a stress-strain curve (see FIG. 1) is termed the Young's modulus. The Young's modulus represents a measure of the hair's spring-like structure (elasticity). The Young's modulus region of the curve is often termed the linear region (sometimes the elastic region). The mean Young's modulus for the hair swatches treated according to the above protocols was determined and the results are summarized in the table below and graphically presented in FIG. 2(a) and FIG. 2(b).

| | N | Mean | Std Dev | Std Err Mean | Lower 95% | Upper 95% |
|---|---|---|---|---|---|---|
| A1 | 47 | 754.3 | 171.4 | 25.0 | 703.4 | 804.6 |
| A2 | 42 | 789.6 | 232.3 | 35.8 | 717.2 | 862.0 |
| A3 | 45 | 953.4 | 170.2 | 25.4 | 902.3 | 1004.5 |

| | N | Mean | Std Dev | Std Err Mean | Lower 95% | Upper 95% |
|---|---|---|---|---|---|---|
| B1 | 47 | 789.2 | 215.7 | 31.5 | 752.9 | 852.6 |
| B2 | 47 | 712.1 | 162.3 | 23.7 | 664.4 | 759.7 |
| B3 | 50 | 757.9 | 203.2 | 28.7 | 700.1 | 815.6 |

The data was statistically analyzed according to the Tukey-Kramer method, a well-known, single-step multiple comparison statistical analysis to find means that are significantly (statistically) different from each other. The mean for A3 was significantly (statistically) higher than the mean of A1 and A2. The means for A1 and A2, however, were not significantly (statistically) different from one another. Similarly, the mean for B1 was higher than the mean for B2 and B3, although the differences between B1, B2, and B3 was not considered statistically different according the Tukey-Kramer method The results illustrate that hair treated according to the method of the instant disclosure exhibit higher Young's modulus mean values than hair treated according to the protocols of A1 and B1, and A2 and B2.

Break Stress Testing

Figure 3A:
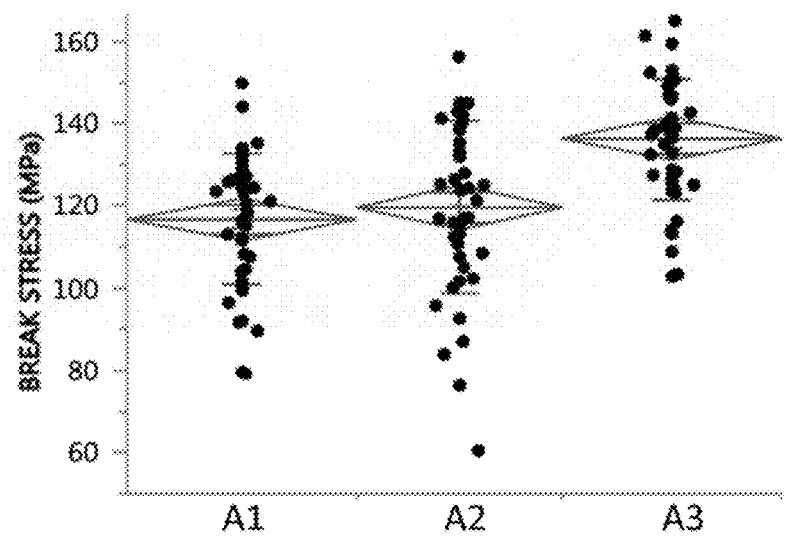
FIG. 3(a) is a graph showing the break stress of hair treated with only a chemical relaxer composition (A1), hair treated according to a commercially available method (A2), and hair treated according to the instant disclosure (A3)
Figure 3B:
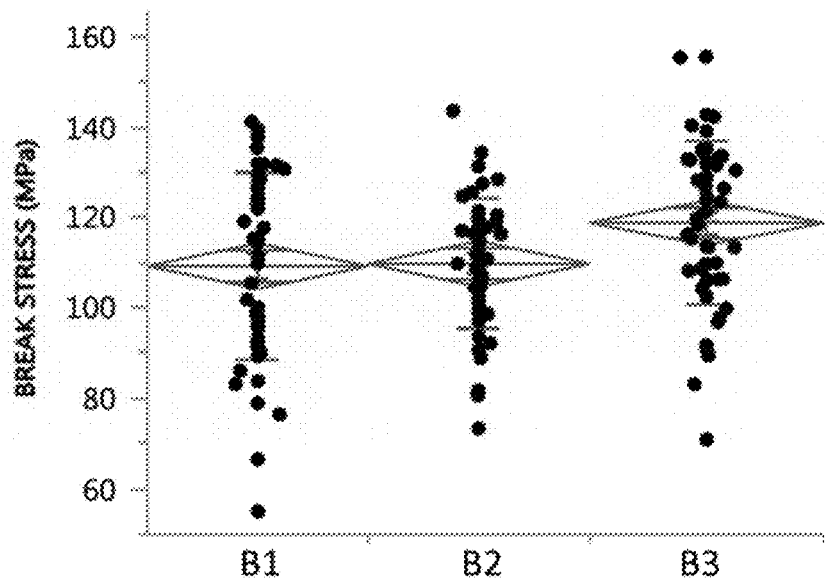
FIG. 3(b) is a graph showing the Young's modulus (the elastic modulus) of hair treated with only a guanidine based chemical relaxer composition (B1), hair treated according to a commercially available method (B2), and hair treated according to the instant disclosure (B3).

The break stress represents the force/area needed to break the hair fiber. A higher break stress represents a stronger and stiffer hair fiber. The hair swatches treated according to protocols A1, A2, and A3 (above) were subjected to break stress testing. The results are summarized in the table below and graphically presented in FIG. 3(a) and FIG. 3(b).

| | N | Mean | Std Dev | Std Err Mean | Lower 95% | Upper 95% |
|---|---|---|---|---|---|---|
| A1 | 47 | 116.7 | 16.0 | 2.3 | 112.0 | 121.4 |
| A2 | 42 | 119.6 | 21.0 | 3.2 | 113.1 | 126.2 |
| A3 | 45 | 136.3 | 14.8 | 2.2 | 131.9 | 140.8 |

| | N | Mean | Std Dev | Std Err Mean | Lower 95% | Upper 95% |
|---|---|---|---|---|---|---|
| B1 | 47 | 109.3 | 20.5 | 3.0 | 103.3 | 115.3 |
| B2 | 47 | 109.8 | 14.3 | 2.1 | 105.6 | 114.0 |
| B3 | 50 | 118.9 | 18.2 | 2.6 | 113.7 | 124.0 |

The data was statistically analyzed according to the Tukey-Kramer method. The mean for A3 was significantly (statistically) higher than the mean of A1 and A2. The mean for A1 and A2, however, were not significantly (statistically) different from one another. Similarly, the mean for B1 was higher than the mean for B2 and B3, although the differences between B1, B2, and B3 were not shown to be statistically significant according the Tukey-Kramer method. The results illustrate that hair treated according to the method of the instant disclosure exhibit higher break stress mean values than hair treated according to the protocols of A1 and B1, and A2 and B2.

Differential Scanning Calorimetry (DCS)

DSC can be a tool for investigating the structural characteristics of hair fibers. Keratin undergoes detectable transformations at various temperatures. Changes in these transformation temperatures can be used to estimate how a particular hair-treatment may influence hair fibers. In the instant case, DSC was used to measure the denaturation temperature ($T_d$) and denaturation enthalpy ($\Delta H$) of hair fibers. Denaturation temperature ($T_d$) has been used as a representation of the thermal stability of hair fibers, which is influenced, at least in part, by the cross-link density of the matrix (intermediate filament associated proteins, IFAP). Thermal stability ($T_d$) and its relationship in determining the thermal stability of hair fibers is established in the literature.

The interpretation of denaturation enthalpy ($\Delta H$) in the context of hair fibers is much more complex and does not necessarily follow the trend for denaturation temperature ($T_d$). Denaturation enthalpy ($\Delta H$) is thought to reflect the relative amount of crystalline/ordered proteins within a hair fiber, and therefore may be used to estimate structural integrity of the α-helical materials (intermediate filaments, IF).

Testing was carried out on hair swatches treated according to protocols described above (A1, A2, A3, B1, B2, and B3). Testing was also carried out using malonic acid in the hair-treatment composition instead of maleic acid, but malonic acid did not perform as well as maleic acid in the DSC testing. It was found that the denaturation temperature ($T_d$) for hair treated according to the instant disclosure using maleic acid (according to protocol A3 and B3) was significantly higher than the denaturation temperature ($T_d$) for hair treated according to according to A1 and A2, and B1 and B2. With respect to denaturation enthalpy ($\Delta H$), the data show that the denaturation enthalpy ($\Delta H$) for A2 was significantly higher than for both A1 and A3, but there was no significant difference in denaturation enthalpy ($\Delta H$) between B1, B2, and B3.

The results from the DSC testing, in particular, the denaturation temperature ($T_d$) data, suggest that hair treated according to the instant disclosure (A3 and B3) has greater thermal stability than hair treated according to A1 and A2, and B1 and B2.

The foregoing description illustrates and describes the disclosure. Additionally, the disclosure shows and describes only the preferred embodiments but, as mentioned above, it is to be understood that it is capable to use in various other combinations, modifications, and environments and is capable of changes or modifications within the scope of the invention concepts as expressed herein, commensurate with the above teachings and/or the skill or knowledge of the relevant art. The embodiments described herein above are further intended to explain best modes known by applicant and to enable others skilled in the art to utilize the disclosure in such, or other, embodiments and with the various modifications required by the particular applications or uses thereof. Accordingly, the description is not intended to limit the invention to the form disclosed herein. Also, it is intended to the appended claims be construed to include alternative embodiments.

As used herein, the terms "comprising," "having," and "including" (or "comprise," "have," and "include") are used in their open, non-limiting sense.

The terms "a," "an," and "the" are understood to encompass the plural as well as the singular.

Thus, the term "a mixture thereof" also relates to "mixtures thereof." Throughout the disclosure, the term "a mixture thereof" is used, following a list of elements as shown in the following example where letters A-F represent the elements: "one or more elements selected from the group consisting of A, B, C, D, E, F, and a mixture thereof." The term, "a mixture thereof" does not require that the mixture include all of A, B, C, D, E, and F (although all of A, B, C, D, E, and F may be included). Rather, it indicates that a mixture of any two or more of A, B, C, D, E, and F can be included. In other words, it is equivalent to the phrase "one or more elements selected from the group consisting of A, B, C, D, E, F, and a mixture of any two or more of A, B, C, D, E, and F."

Likewise, the term "a salt thereof" also relates to "salts thereof." Thus, where the disclosure refers to "an element selected from the group consisting of A, B, C, D, E, F, a salt thereof, and a mixture thereof," it indicates that that one or more of A, B, C, D, and F may be included, one or more of a salt of A, a salt of B, a salt of C, a salt of D, a salt of E, and a salt of F may be include, or a mixture of any two of A, B, C, D, E, F, a salt of A, a salt of B, a salt of C, a salt of D, a salt of E, and a salt of F may be included.

The salts referred to throughout the disclosure may include salts having a counter-ion such as an alkali metal, alkaline earth metal, or ammonium counterion. This list of counterions, however, is non-limiting.

The expression "one or more" means "at least one" and thus includes individual components as well as mixtures/combinations.

Other than in the operating examples, or where otherwise indicated, all numbers expressing quantities of ingredients and/or reaction conditions are to be understood as being modified in all instances by the term "about," meaning within +/−5% of the indicated number.

Some of the various categories of components identified for the hair-treatment compositions may overlap. For example, overlap may exist between some thickening agents and some cationic polymers. In such cases where overlap may exist and the hair-treatment composition includes both components (or the hair-treatment composition includes more than two components that overlap), an overlapping compound does not represent more than one component. For example, a homopolymer of methyl quaternized dimethylaminoethyl methacrylate crosslinked by a crosslinking agent may be considered both a cationic polymer and a thickening agent. If a particular hair-treatment composition includes both a cationic polymer component and a thickening agent component, a single homopolymer of methyl quaternized dimethylaminoethyl methacrylate crosslinked by a crosslinking agent will serve as only the cationic polymer or only the thickening agent (the compound does not serve as both the cationic polymer and the thickening agent).

All percentages, parts and ratios herein are based upon the total weight of the compositions of the present invention, unless otherwise indicated.

"Keratinous substrates" as used herein, includes, but is not limited to keratin fibers such as hair and/or scalp on the human head.

"Conditioning" as used herein means imparting to one or more hair fibers at least one property chosen from combability, moisture-retentivity, luster, shine, and softness. The state of conditioning can be evaluated by any means known in the art, such as, for example, measuring, and comparing, the ease of combability of the treated hair and of the untreated hair in terms of combing work (gm-in), and consumer perception.

The term "treat" (and its grammatical variations) as used herein refers to the application of the compositions of the present disclosure onto the surface of keratinous substrates such as hair. The term "treat," and its grammatical variations, relates to contacting hair with the hair-treatment compositions of the present disclosure.

The term "stable" as used herein means that the composition does not exhibit phase separation and/or crystallization for a period of time, for example, for at least 1 day (24 hours), one week, one month, or one year.

"Volatile", as used herein, means having a flash point of less than about 100° C.

"Non-volatile", as used herein, means having a flash point of greater than about 100° C.

All ranges and values disclosed herein are inclusive and combinable. For examples, any value or point described herein that falls within a range described herein can serve as a minimum or maximum value to derive a sub-range, etc. Furthermore, all ranges provided are meant to include every specific range within, and combination of sub-ranges between, the given ranges. Thus, a range from 1-5, includes specifically 1, 2, 3, 4 and 5, as well as sub ranges such as 2-5, 3-5, 2-3, 2-4, 1-4, etc.

The term "substantially free" or "essentially free" as used herein means that there is less than about 5% by weight of a specific material added to a composition, based on the total weight of the compositions. Nonetheless, the compositions may include less than about 3 wt. %, less than about 2 wt. %, less than about 1 wt. %, less than about 0.5 wt. %, less than about 0.1 wt. %, or none of the specified material.

The term "essentially anhydrous" or "substantially anhydrous" as used herein, for example, in the context of an "essentially anhydrous hair-treatment composition" or a "substantially anhydrous hair-treatment composition" means that the composition includes less than about 5% by weight of water. Nonetheless, the composition may include less than about 4 wt. %, less than about 3 wt. %, less than about 2 wt. %, less than about 1 wt. %, less than about 0.5 wt. %, less than about 0.1 wt. % of water, less than about 0.05 wt. % water, or less than 0.01 wt. % water.

All publications and patent applications cited in this specification are herein incorporated by reference, and for any and all purposes, as if each individual publication or patent application were specifically and individually indicated to be incorporated by reference. In the event of an inconsistency between the present disclosure and any publications or patent application incorporated herein by reference, the present disclosure controls.

The invention claimed is:

1. A method for treating hair comprising:
   A. applying a chemical relaxer composition to the hair and relaxing the hair;
   B. rinsing the chemical relaxer composition from the hair;
   C. applying a neutralizing composition to the hair within 15 minutes from rinsing the chemical relaxer composition from the hair, the neutralizing composition comprising:
      a. at least 0.5 to about 8 wt. % of maleic acid and/or a salt thereof, based on the total weight of the neutralizing composition;
      b. about 0.2 to about 5 wt. % of monoethanolamine, based on the total weight of the neutralizing composition; and
      c. water;
         wherein the ratio of maleic acid and/or a salt thereof to monoethanolamine in the neutralizing composition is about 1:1 to about 5:1;
   D. allowing the neutralizing composition to remain on the hair for 8 to 12 minutes;
   E. after the neutralizing composition has remained on the hair for 8 to 12 minutes, without rinsing the neutralizing composition from the hair, applying a neutralizing conditioner to the hair, the neutralizing conditioner comprising:
      i. at least 0.5 to about 8 wt. % of maleic acid, based on the total weight of the neutralizing conditioner;
      ii. about 0.2 to about 5 wt. % of monoethanolamine, based on the total weight of the neutralizing conditioner;
      iii. about 0.5 to about 5 wt. % of one or more cationic surfactants, based on the total weight of the neutralizing conditioner;
      iv. about 0.5 to about 20 wt. % of one or more fatty compounds;
      v. about 0.5 to about 20 wt. % of one or more water-soluble solvents, based on the total weight of the neutralizing conditioner; and
      vi. water;
         wherein the ratio of maleic acid to monoethanolamine in the neutralizing conditioner is about 1:1 to about 5:1 (maleic acid:monethanolamine);
   F. allowing the neutralizing conditioner to remain on the hair for 8 to 12 minutes;
   G. rinsing the neutralizing conditioner and the neutralizing composition from the hair;
   H. applying a shampoo to the hair within 15 minutes from rinsing the neutralizing conditioner and the neutralizing composition from the hair; and
   I. rinsing the shampoo from the hair.

2. The method of claim 1, wherein the ratio of maleic acid and/or a salt thereof to monoethanolamine in the neutralizing composition is about 1:1 to about 3:1.

3. The method of claim 1, wherein the neutralizing composition comprises about 1 to about 5 wt. % of the maleic acid and/or a salt thereof, based on the total weight of the neutralizing composition.

4. The method of claim 1, wherein the ratio of maleic acid and/or a salt thereof to monoethanolamine in the neutralizing conditioner is about 1:1 to about 3:1.

5. The method of claim 1, wherein the neutralizing conditioner comprises about 1 to about 5 wt. % of the maleic acid and/or a salt thereof, based on the total weight of the neutralizing conditioner.

6. The method of claim 1, wherein the neutralizing composition comprises about 0.2 to about 3 wt. % of monoethanolamine, based on the total weight of the neutralizing composition.

7. The method of claim 1, wherein the neutralizing conditioner comprises about 0.2 to about 3 wt. % of monoethanolamine, based on the total weight of the neutralizing conditioner.

8. The method of claim 1, wherein the neutralizing composition comprises about 85 to about 98 wt. % water.

9. The method of claim 1, wherein the neutralizing conditioner comprises about 60 to about 90 wt. % water.

10. The method of claim 1, wherein the one or more cationic surfactants are selected from the group consisting of cetrimonium chloride, cetrimonium methosulfate, stearimonium chloride, behentrimonium chloride, behentrimonium methosulfate, behenamidopropyltrimonium methosulfate, stearamidopropyltrimonium chloride, arachidtrimonium chloride, distearyldimonium chloride, dicetyldimonium chloride, tricetylmonium chloride, oleamidopropyl dimethylamine, linoleamidopropyl dimethylamine, stearamidopropyl dimethylamine, isostearamidopropyl dimethylamine, oleyl hydroxyethyl imidazoline, stearamidopropyldimethylamine, behenamidopropyldimethylamine, behenamidopropyldiethylamine, behenamidoethyldiethyl-amine, behenamidoethyldimethylamine, arachidamidopropyldimethylamine, arachidamido-propyidiethylamine, arachidamidoethyidiethylamine, arachidamidoethyidimethylamine, quaternium-91, and a mixture thereof.

11. The method of claim 1, wherein the one or more fatty compounds are selected from the group consisting of oils, waxes, butter, alkanes, fatty alcohols, fatty acids, fatty alcohol derivatives, fatty acid derivatives, esters of fatty alcohols, hydroxy-substituted fatty acids, waxes, triglyceride compounds, lanolin, ceramide, and a mixture thereof.

12. The method of claim 1, wherein the total amount of the one or more fatty compounds is about 1 wt. % to about 10 wt. %, based on the total weight of the neutralizing conditioner.

13. The method of claim 1, wherein the one or more water-soluble solvents are selected from the group consisting of polyhydric alcohols, glycol ethers, $C_{1-4}$ alcohols, and a mixture thereof.

14. The method of claim 1, wherein the total amount of water-soluble solvents in the neutralizing conditioner are about 1 wt. % to about 10 wt. %, based on the total weight of the neutralizing conditioner.

15. The method of claim 1, wherein the method comprises increasing a mean Young's modulus of the hair by at least 10% relative to hair treated with only a chemical relaxer composition.

16. The method of claim 1, wherein the method comprises increasing a mean break stress of the hair by at least 10% relative to hair treated with only a chemical relaxer composition.

17. A method for treating hair comprising:
   A. applying a chemical relaxer composition to the hair and relaxing the hair;
   B. rinsing the chemical relaxer composition from the hair;
   C. applying a neutralizing composition to the hair within 15 minutes from rinsing the chemical relaxer composition from the hair, the neutralizing composition comprising:
      a. at least 0.5 to about 8 wt. % of maleic acid and/or a salt thereof, based on the total weight of the neutralizing composition;
      b. about 0.2 to about 5 wt. % of monoethanolamine, based on the total weight of the neutralizing composition; and
      c. about 85 to about 98 wt. % of water;
         wherein the ratio of maleic acid and/or a salt thereof to monoethanolamine in the neutralizing composition is about 1:1 to about 3:1;
   D. allowing the neutralizing composition to remain on the hair for about 10 minutes;
   E. after the neutralizing composition has remained on the hair for about 10 minutes, without rinsing the neutralizing composition from the hair, applying a neutralizing conditioner to the hair, the neutralizing conditioner comprising:
      i. about 1 to about 5 wt. % of maleic acid, based on the total weight of the neutralizing conditioner;
      ii. about 0.2 to about 3 wt. % of monoethanolamine, based on the total weight of the neutralizing conditioner;
      iii. about 0.5 to about 5 wt. % of one or more cationic surfactants, based on the total weight of the neutralizing conditioner;
      iv. about 0.5 to about 20 wt. % of one or more fatty compounds;
      v. about 0.5 to about 20 wt. % of one or more water-soluble solvents, based on the total weight of the neutralizing conditioner; and
      vi. about 60 to about 90 wt. % water, based on the total weight of the neutralizing conditioner;
         wherein the ratio of maleic acid to monoethanolamine in the neutralizing conditioner is about 1:1 to about 3:1;
   F. allowing the neutralizing conditioner to remain on the hair for about 10 minutes;
   G. rinsing the neutralizing conditioner and the neutralizing composition from the hair;
   H. applying a shampoo to the hair within 15 minutes from rinsing the neutralizing conditioner and the neutralizing composition from the hair; and
   I. rinsing the shampoo from the hair.

18. The method of claim 17, wherein the one or more cationic surfactants are selected from the group consisting of cetrimonium chloride, cetrimonium methosulfate, stearimonium chloride, behentrimonium chloride, behentrimonium methosulfate, behenamidopropyltrimonium methosulfate, stearamidopropyltrimonium chloride, arachidtrimonium chloride, distearyldimonium chloride, dicetyldimonium chloride, tricetylmonium chloride, oleamidopropyl dimethylamine, linoleamidopropyl dimethylamine, stearamidopropyl dimethylamine, isostearamidopropyl dimethylamine, oleyl hydroxyethyl imidazoline, stearamidopropyldimethylamine, behenamidopropyldimethylamine, behenamidopropyldiethylamine, behenamidoethyldiethyl-amine, behenamidoethyldimethylamine, arachidamidopropyldimethylamine, arachidamido-propyidiethylamine, arachidamidoethyidiethylamine, arachidamidoethyidimethylamine, quaternium-91, and a mixture thereof.

19. The method of claim 17, wherein the one or more fatty compounds are selected from the group consisting of oils, waxes, butter, alkanes, fatty alcohols, fatty acids, fatty alcohol derivatives, fatty acid derivatives, esters of fatty alcohols, hydroxy-substituted fatty acids, waxes, triglyceride compounds, lanolin, ceramide, and a mixture thereof.

20. The method of claim 17, wherein the one or more water-soluble solvents are selected from the group consisting of polyhydric alcohols, glycol ethers, $C_{1-4}$ alcohols, and a mixture thereof.

21. The method of claim 17, wherein the method comprises increasing a mean Young modulus of the hair by at least 10% relative to hair treated with only a chemical relaxer composition.

22. The method of claim 17, wherein the method comprises increasing a mean break stress of the hair by at least 10% relative to hair treated with only a chemical relaxer composition.

* * * * *